United States Patent
Tibbitt et al.

(10) Patent No.: US 11,262,361 B2
(45) Date of Patent: Mar. 1, 2022

(54) SELECTIVE CAPTURE AND RELEASE OF RARE MAMMALIAN CELLS USING PHOTODEGRADABLE HYDROGELS IN A MICROFLUIDIC PLATFORM

(71) Applicant: THE GENERAL HOSPITAL CORPORATION, Boston, MA (US)

(72) Inventors: Mark W. Tibbitt, Boulder, CO (US); Kristi S. Anseth, Boulder, CO (US); April M. Kloxin, Boulder, CO (US); Mehmet Toner, Boulder, CO (US); John Oakey, Boston, MA (US); Ajay Shah, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 314 days.

(21) Appl. No.: 14/905,460

(22) PCT Filed: Jul. 18, 2014

(86) PCT No.: PCT/US2014/047195
§ 371 (c)(1),
(2) Date: Jan. 15, 2016

(87) PCT Pub. No.: WO2015/010019
PCT Pub. Date: Jan. 22, 2015

(65) Prior Publication Data
US 2016/0153999 A1  Jun. 2, 2016

Related U.S. Application Data

(60) Provisional application No. 61/847,896, filed on Jul. 18, 2013.

(51) Int. Cl.
*G01N 33/574* (2006.01)
*A61K 47/34* (2017.01)
(Continued)

(52) U.S. Cl.
CPC ... *G01N 33/57492* (2013.01); *A61K 41/0028* (2013.01); *A61K 47/34* (2013.01);
(Continued)

(58) Field of Classification Search
None
See application file for complete search history.

(56) References Cited

U.S. PATENT DOCUMENTS

| 4,945,050 A | 7/1990 | Sanford et al. |
| 5,550,178 A | 8/1996 | Desai et al. |

(Continued)

FOREIGN PATENT DOCUMENTS

| WO | 2007082302 A2 | 7/2007 |
| WO | 2010132795 A2 | 11/2010 |

OTHER PUBLICATIONS

Fairbanks et al. (Fairbanks, Biomaterials, 2009, 30, 6702-6707) (Year: 2009).*

(Continued)

*Primary Examiner* — Karl J Puttlitz
(74) *Attorney, Agent, or Firm* — Quarles & Brady LLP

(57) ABSTRACT

Disclosed herein are photodegradable hydrogels and associated kits for selectively capturing and releasing cells. The hydrogels result from cross linking in the presence of a photoinitiator (1) a macromer having a polymeric backbone structure, a photo labile moiety, and a first linking moiety, and (2) a cell-binding moiety having a second linking moiety. These two components are cross-linked by a polymerization reaction of the linking moieties to form a photodegradable hydrogel incorporating the cell-binding moiety within the hydrogel. Also disclosed are methods of making the hydrogels, and methods of using the hydrogels for selectively capturing and releasing cells and for detecting cells in a fluid. Such methods can be used to detect the (Continued)

presence and quantity of certain rare cell types in a biological fluid.

15 Claims, 4 Drawing Sheets

(51) Int. Cl.
    *A61K 41/00* (2020.01)
    *C12M 1/00* (2006.01)
    *B01L 3/00* (2006.01)
    *C08F 222/22* (2006.01)
    *G01N 33/531* (2006.01)
    *G01N 33/543* (2006.01)
    *G01N 33/569* (2006.01)

(52) U.S. Cl.
    CPC ...... *B01L 3/502761* (2013.01); *C08F 222/22* (2013.01); *C12M 47/02* (2013.01); *C12M 47/04* (2013.01); *G01N 33/531* (2013.01); *G01N 33/54366* (2013.01); *G01N 33/56966* (2013.01); *B01L 2200/0647* (2013.01); *B01L 2300/16* (2013.01)

(56) References Cited

U.S. PATENT DOCUMENTS

| | | | |
|---|---|---|---|
| 5,665,582 A | 9/1997 | Kausch et al. | |
| 5,766,908 A | 6/1998 | Klein et al. | |
| 8,343,710 B1* | 1/2013 | Anseth | C08F 220/34 430/281.1 |
| 2003/0228637 A1 | 12/2003 | Wang | |
| 2005/0037343 A1 | 2/2005 | Fagnani et al. | |
| 2006/0014137 A1 | 1/2006 | Ghosh et al. | |
| 2006/0040274 A1* | 2/2006 | Tsinberg | G01N 33/54353 435/6.19 |
| 2006/0134599 A1 | 6/2006 | Toner et al. | |
| 2006/0141045 A1* | 6/2006 | Bhatt | A61K 9/1641 424/489 |
| 2006/0159663 A1 | 7/2006 | Lu et al. | |
| 2007/0099207 A1 | 5/2007 | Fuchs et al. | |
| 2007/0148768 A1 | 6/2007 | Liao et al. | |
| 2007/0231851 A1 | 10/2007 | Toner et al. | |
| 2009/0324675 A1 | 12/2009 | Gundatillake et al. | |
| 2011/0294187 A1 | 12/2011 | Toner | |
| 2012/0270209 A1 | 10/2012 | Shah et al. | |
| 2014/0031285 A1 | 1/2014 | Anseth et al. | |
| 2015/0125879 A1* | 5/2015 | Li | G01N 33/54366 435/7.23 |

OTHER PUBLICATIONS

Wang et al. ("Wang", Macromolecular Biosci., 2011, 11, 100-110 (Year: 2011).*
Kloxin et al., Science. Apr. 3, 2009; 324(5923): 59-63 (Year: 2009).*
Cheung et al., Bioconjugate Chem. 2006, 17, 1036-1042 (Year: 2006).*
Shimoni et al., ACS Nano, vol. 6, No. 2, 1463-1472, 2012 (Year: 2012).*
Braun, et al., Circulating Tumor Cells in Metastatic Breast Cancer—Toward Individualized Treatment?, The New England Journal of Medicine, 2004, 351:824-826.
Cooperstein, et al., Biological Cell Detachment from Poly(N-isopropyl acrylamide) and Its Applications, Langmuir, 2010, 26(11):7695-7707.
Evanko, Microfluidics and a Garden Hose, Nature Methods, 2008, 5(2):124.
Hume, et al., Inducing Local T-cell Apoptosis with Anti-Fas-Functionalized Polymeric Coatings Fabricated via Surface-nitiated Photopolymerizations, Biomaterials, 2010, 31(12):3166-3174.
Pappas, et al., Cellular Separations: A Review of New Challenges in Analytical Chemistry, Analytica Chimica Acta, 2007, 601(1):26-35.
Wang, et al., Open-Tubular Capillary Cell Affinity Chromatography: Single and Tandem Blood Cell Separation, Anal. Chem., 2008, 80(6):2118-2124.
Cheng, et al., A Microfluidic Device for Practical Label-Free CD4+ T Cell Counting of HIV-Infected Subjects, Lab Chip, 2007, 7(2):170-178.
Cristofanilli, et al., Circulating Tumor Cells, Disease Progression, and Survival in Metastatic Breast Cancer, The New England Journal of Medicine, 2004,351:781-791.
Fairbanks, et al., Photoinitiated Polymerization of PEG-diacrylate With Lithium phenyl-2,4,6-trimethylbenzoylphosphinate: Polymerization Rate and Cytocompatibility, Biomaterials, 2009, 30(35):6702-6707.
Hatch, et al., Engineered Alginate Hydrogels for Effective Microfluidic Capture and Release of Endothelial Progenitor Cells from Whole Blood, Langmuir, 2011, 27(7):4257-4264.
Kloxin, et al., Photodegradable Hydrogels for Dynamic Tuning of Physical and Chemical Properties, Science, 2009, 324(5923):59-63.
Kloxin, et al., Synthesis of Photodegradable Hydrogels as Dynamically Tunable Cell Culture Platforms, Nat Protoc., 2010, 5(12): 1867-1887.
Machaca, Ca2+ Signaling, Genes and the Cell Cycle, Cell Calcium, 2010, 48(5):243-250.
Maheswaran, et al., Detection of Mutations in EGFR in Circulating Lung-Cancer Cells, The New England Journal of Medicine 2008, 359(4):366-377.
Nagrath, et al., Isolation of Rare Circulating Tumour Cells in Cancer Patients by Microchip Technology, Nature, 2007, 450(7173):1235-1239.
Shah, et al., A Biopolymer System for Cell Recovery from Microfluidic Cell Capture Devices, Anal. Chem., 2012, 84(8):3682-3688.
Shin, et al., Photolabile Micropatterned Surfaces for Cell Capture and Release, Chemical Communications, 2011, 47(43):11942-11944.
Stott, et al., Isolation and Characterization of Circulating Tumor Cells from Patients with Localized and Metastatic Prostate Cancer, Sci. Transl. Med., 2010, 2(25):25ra23.
Stott, et al., Isolation of Circulating Tumor Cells Using a Microvortex-Generating Herringbone-Chip, PNAS, 2010, 107(43):18392-18397.
Tibbitt, et al., Mechanical Properties and Degradation of Chain and Step-Polymerized Photodegradable Hydrogels, Macromolecules, 2013, 46:2785-2792.
International Search Report and Written Opinion dated Oct. 23, 2014 in connection with PCT/US2014/047195.

* cited by examiner

SELECTIVE CAPTURE AND RELEASE OF RARE MAMMALIAN CELLS USING PHOTODEGRADABLE HYDROGELS IN A MICROFLUIDIC PLATFORM

CROSS-REFERENCE TO RELATED APPLICATIONS

This application is a 371 application of PCT/US2014/047195 filed Jul. 18, 2014 which claims the benefit of U.S. Provisional Application No. 61/847,896 filed on Jul. 18, 2013, which is incorporated by reference herein in its entirety.

STATEMENT REGARDING FEDERALLY SPONSORED RESEARCH OR DEVELOPMENT

This invention was made with government support under grant numbers EB012493 and EB002503 awarded by the National Institutes of Health and grant number DMR 1006711D awarded by the National Science Foundation. The Government has certain rights in this invention.

BACKGROUND

Microfluidic devices with affinity labels enable unique opportunities for the capture and sorting of mammalian cells from complex aqueous solutions, such as culture medium or whole blood, with minimal preprocessing.[1] For example, antibody-functionalized microfluidic devices have been employed to capture EpCAM-expressing cancer cells spiked into whole blood[2] and CD4+ T-cells from HIV+ subjects.[3] A traditional limitation of microfluidic devices is that they can only process nanoliter to microliter scale volumes; however, recent work from Toner et al. has demonstrated that adjustments to device geometry enable the processing of milliliters of whole blood to capture exceptionally rare circulating tumor cells (CTCs).[2,4,5] Further improvements on the geometry of antibody-functionalized microfluidic capture devices have facilitated clinical applications in cancer diagnostics through the capture of CTCs directly from patient blood.[6,7]

Despite these advances, capture devices are still limited in the ability to analyze and process captured cells downstream. Current methods to confirm the identity of captured cells are confined to on-chip labeling, e.g., FISH or immunocytochemistry, owing to the inability to remove desired cells from the capture surface. Developing materials that enable selective capture and release of individual cells to allow genome-wide analysis of single cells, in vitro culture, and in vivo testing will enable a better understanding of rare cell populations such as circulating tumor cells and certain stem cell populations, as well as better point-of-care diagnostics.

Initial work to recover cells from capture surfaces has focused on the use of chemical or mechanical dislocation. In these examples, chemical gradients or shear forces were employed to disrupt cell-material interactions and to elute captured cells.[8,9] However, strong chemical treatment and shear forces are known to damage cells or at a minimum rapidly alter gene expression, limiting the application of these techniques.[10] More recent studies have focused on the fabrication of microfluidic capture devices with phase changing materials, through the application of temperature,[11] ions,[12] or enzymes,[10] that enable the disruption of cell-material interactions and subsequent recovery of captured cells. Specifically, Murthy et al. employed sacrificial alginate layers to capture endothelial progenitor cells from blood that could be released through the treatment and dissolution of the alginate capture layer with $Ca^{2+}$ ions.[12] This treatment is limited in that it cannot be conducted in the presence of calcium chelating ligands, e.g., EDTA and citrates, and calcium treatment can alter cell signaling on short time scales.[10,13]

The use of alginate layers has been extended by Toner et al. to enable capture of cancer cells and their subsequent release with alginate lysase.[10] While this method is cytocompatibile and enables highly efficient recovery of captured cells, it is still limited in that the whole capture surface becomes disrupted with the application of the enzyme and the experimenter is unable to recover selected cells as the whole population of captured cells is released. Captured cell populations are often heterogeneous. For example, circulating tumor cells from a given tumor can have different genotypes and rare stem cells can exist in asymmetric states. Therefore, individual cell release and recovery is desired to better analyze the cells that are captured with these devices and to characterize fully rare cell populations. This ability requires spatial control over cell release from the capture surface, which is possible with light-based release mechanisms, such as those disclosed herein.

BRIEF DESCRIPTION

Here, we present the fabrication of microfluidic capture devices with antibody-functionalized, thin film, photodegradable hydrogels as the capture surface. Photolabile, poly (ethylene glycol) (PEGdiPDA) based hydrogels are polymerized within microfluidic chambers using visible wavelength photoinitiation, which allows for longwave UV light induced gel erosion with both spatial and temporal precision. Acrylated-NeutrAvidin is included in the hydrogel formulation to facilitate subsequent functionalization with a variety of biotinylated antibodies, for example anti-EpCAM. Mammalian cells are selectively captured on the surface of antibody-functionalized gels within the microfluidic devices and subsequently released with cytocompatible, UV light exposure. This platform offers the unique ability to capture and selectively release mammalian cells toward the individual culture and analysis of circulating tumor cells and isolation of rare stem cells.

Accordingly, in a first aspect, the disclosure encompasses a photodegradable hydrogel for selectively capturing and releasing cells. The hydrogel is produced by reacting in the presence of light: (a) a macromer having the chemical structure: L-P-B-P-L; wherein (i) L is a first linking moiety terminating with —$CH_xCH_y$, wherein the bond between the two carbon atoms is a covalent double or triple bond capable of taking part in an addition polymerization reaction, and wherein x is 0 or 1 and y is 1 or 2; (ii) P is a photolabile moiety; and (iii) B is a backbone structure comprising one or more repeating units that may be the same or different; (b) a cell-binding moiety attached to a second linking moiety terminating with (i) —$CH_xCH_y$, wherein the bond between the two carbon atoms is a covalent double or triple bond capable of taking part in an addition polymerization reaction, and wherein x is 0 or 1 and y is 1 or 2, or (ii) —SH, wherein the —SH is capable of taking part in one or more of chain-growth polymerization, step-growth polymerization, or mixed-mode polymerization; and (c) a photoinitiator capable of producing free radicals in the presence of light.

The free radicals produced in the presence of light initiate a polymerization reaction, whereby the first linking moiety of the L groups of the macromer and the second linking moiety of the cell binding moiety are incorporated into polymer chains, whereby the macromer is cross-linked to form a hydrogel and the cell-binding moiety is incorporated into the hydrogel.

In some embodiments, the first linking moiety, the second linking moiety, or both may include a terminal acrylate group.

In some embodiments, the photolabile moiety has the chemical structure:

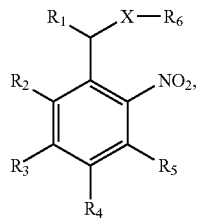

where X is O, N or S; $R_1$ is selected from the group consisting of: hydrogen, straight-chain or branched C1-C10 alkyl, aryl, alkoxy, aryloxy or carboxy groups in which one or more carbon atoms can be independently optionally substituted with one or more heteroatoms, and one or more hydrogen atoms can be independently optionally substituted with hydroxyl, halogen or oxygen atoms.

$R_2$-$R_6$ are independently selected from the group consisting of: hydrogen; one or more polymerizable groups, one or more reactive end groups; straight chain, branched or cyclic C1-C20 alkyl, alkenyl, alkynyl groups in which one or more of the carbon atoms are optionally substituted with non-hydrogen substituents and wherein one or more C, CH or $CH_2$ moiety can be replaced with an oxygen atom, a nitrogen atom, an NR' group, or a S atom; and an optionally substituted aromatic or non-aromatic ring structure, wherein two or more R groups can be linked to form one or more rings which can contain one or more of the same or different heteroatoms.

One or more R groups can be optionally substituted with one or more substituent groups selected from halogens; nitro groups; cyano groups; isocyano groups; thiocyano groups; isothiocyano groups; azide groups; —$SO_2$ groups; —$OSO_3H$ groups; one or more optionally substituted straight-chain, branched or cyclic alkyl, alkenyl or alkynyl groups; OR'; —CO—OR'; —O—CO—R'; —N(R')$_2$; —CO—N(R')$_2$; —NR'—CO—OR'; —SR'; —SOR'; —$SO_2$—R'; —$SO_3$R'; —$SO_2$N(R')$_2$; —P(R')$_2$; —$OPO_3$(R')$_2$; and —Si(R')$_3$ wherein each R', independent of other R' in the substituent group can be a hydrogen, an optionally substituted straight-chain, branched or cyclic alkyl, alkenyl or alkynyl group wherein one or more C, CH or $CH_2$ groups therein can be replaced with an O atom, N atom, S atom or —NH group; an optionally substituted aromatic group, two or more R' groups can be linked together to form a ring which may contain one or more of the same or different heteroatoms.

R' can in turn be optionally substituted with one or more groups selected from the group consisting of halogens, nitro groups; cyano groups; isocyano groups; thiocyano groups; isothiocyano groups; azide groups; —$SO_2$ groups; —$OSO_3H$ groups; straight-chain, branched or cyclic alkyl, alkenyl or alkynyl groups; halogenated alkyl groups; hydroxyl groups; alkoxy groups; carboxylic acid and carboxylic ester groups; amine groups; carbamate groups, thiol groups, thioether and thioester groups; sulfoxide groups, sulfone groups; sulfide groups; sulfate and sulfate ester groups; sulfonate and sulfonate ester groups; sulfonamide groups, sulfonate ester groups; phosphine groups; phosphate and phosphate ester groups; phosphonate and phosphonate ester groups; and alkyl-substituted silyl groups.

In some embodiments, the photolabile moiety has the chemical structure:

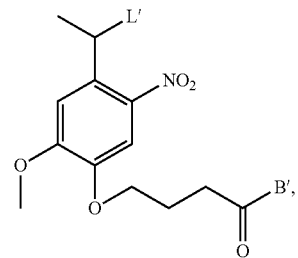

wherein L' is a covalent linkage to the first linking moiety, and wherein B' is a covalent linkage to the backbone structure.

In some embodiments, the backbone structure is selected from the group consisting of poly(ethylene glycol), poly(ethylene oxide), poly(vinyl alcohol), poly(styrene), poly(acrylate), poly(methacrylate), poly(vinylether), poly(urethane), polypropylene, polyester and polyethylene.

In some embodiments, the macromer has the chemical structure:

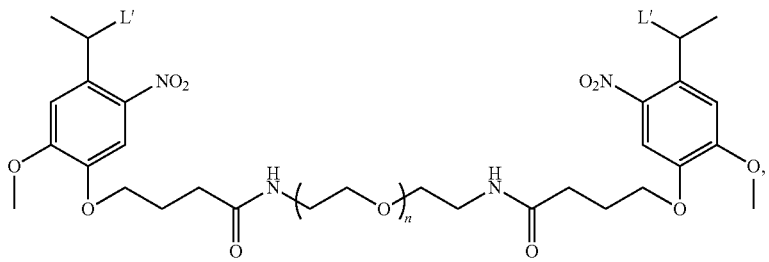

wherein L' is a covalently linkage to the first linking moiety.

In some such embodiments, the macromer has the chemical structure:

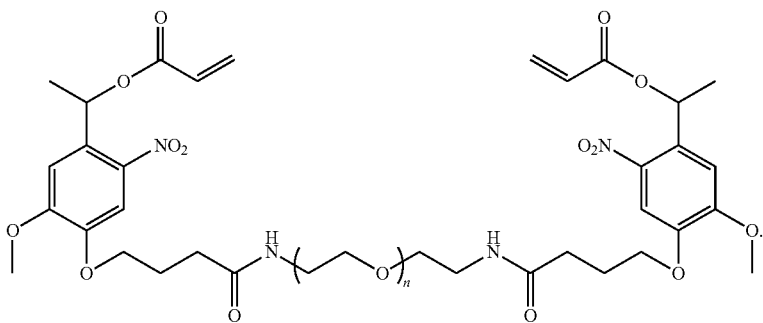

In some embodiments, the cell-binding moiety comprises a hapten-binding moiety. Optionally, the hapten-binding moiety may be selected from the group consisting of biotin-binding moiety, apatamer-binding moiety and glycan-binding moiety. Optionally, the biotin-binding moiety may include avidin or NeutrAvidin.

In some embodiments, the cell-binding moiety is acrylated. In some embodiments, the cell-binding moiety may further include a cell-binding agent, such as an antibody. Optionally, the antibody may be biotinylated. In some embodiments, the antibody may be an antibody which is capable of binding to circulating tumor cells (CTC), including without limitation prostate cancer cells (PC3) and lung cancer A549 cells.

In some embodiments, the antibody is an anti-EpCAM antibody and the CTC is an EpCAM expressing cell.

In some embodiments, the photoinitiator is lithium phenyl-2,4,6-trimethylbenzoylphosphinate (LAP).

In some embodiments, the light is in the visible wavelength range.

In a second aspect, this disclosure encompasses a method of preparing a photodegradable hydrogel for selectively capturing and releasing cells comprising the step of reacting in the presence of light: (a) a macromer having the chemical structure: L-P-B-P-L; wherein (i) L is a first linking moiety terminating with —$CH_xCH_y$, wherein the bond between the two carbon atoms is a covalent double or triple bond capable of taking part in an addition polymerization reaction, and wherein x is 0 or 1 and y is 1 or 2; (ii) P is a photolabile moiety; and (iii) B is a backbone structure comprising one or more repeating units that may be the same or different; (b) a cell-binding moiety attached to a second linking moiety terminating with (i) —$CH_xCH_y$, wherein the bond between the two carbon atoms is a covalent double or triple bond capable of taking part in an addition polymerization reaction, and wherein x is 0 or 1 and y is 1 or 2, or (ii) —SH, wherein the —SH is capable of taking part in one or more of chain-growth polymerization, step-growth polymerization, or mixed-mode polymerization; and (c) a photoinitiator capable of producing free radicals in the presence of light, wherein the free radicals produced initiate an addition polymerization reaction, whereby the first linking moiety of the L groups of the macromer and the second linking moiety of the cell binding moiety are incorporated into polymer chains, whereby the macromer is cross-linked to form a hydrogel and the cell-binding moiety is incorporated into the hydrogel.

In some embodiments, the first linking moiety, the second linking moiety, or both include a terminal acrylate group.

In some embodiments, the photolabile moiety has the chemical structure:

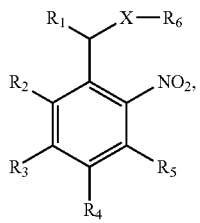

where X is O, N or S; $R_1$ is selected from the group consisting of: hydrogen, straight-chain or branched C1-C10 alkyl, aryl, alkoxy, aryloxy or carboxy groups in which one or more carbon atoms can be independently optionally substituted with one or more heteroatoms, and one or more hydrogen atoms can be independently optionally substituted with hydroxyl, halogen or oxygen atoms.

$R_2$-$R_6$ are independently selected from the group consisting of: hydrogen; one or more polymerizable groups, one or more reactive end groups; straight chain, branched or cyclic C1-C20 alkyl, alkenyl, alkynyl groups in which one or more of the carbon atoms are optionally substituted with non-hydrogen substituents and wherein one or more C, CH or $CH_2$ moiety can be replaced with an oxygen atom, a nitrogen atom, an NR' group, or a S atom; and an optionally substituted aromatic or non-aromatic ring structure, wherein two or more R groups can be linked to form one or more rings which can contain one or more of the same or different heteroatoms.

One or more R groups can be optionally substituted with one or more substituent groups selected from halogens; nitro groups; cyano groups; isocyano groups; thiocyano groups; isothiocyano groups; azide groups; —$SO_2$ groups; —$OSO_3H$ groups; one or more optionally substituted straight-chain, branched or cyclic alkyl, alkenyl or alkynyl groups; OR'; —CO—OR'; —O—CO—R'; —N(R')$_2$; —CO—N(R')$_2$; —NR'—CO—OR'; —SR'; —SOR'; —$SO_2$—R'; —$SO_3$R'; —$SO_2$N(R')$_2$; —P(R')$_2$; —$OPO_3$(R')$_2$; and —Si(R')$_3$ wherein each R', independent of other R' in the substituent group can be a hydrogen, an optionally substituted straight-chain, branched or cyclic alkyl, alkenyl or alkynyl group wherein one or more C, CH or $CH_2$ groups therein can be replaced with an O atom, N atom, S atom or —NH group; an optionally substituted aromatic group, two or more R' groups can be linked together to form a ring which may contain one or more of the same or different heteroatoms.

R' can in turn be optionally substituted with one or more groups selected from the group consisting of halogens, nitro groups; cyano groups; isocyano groups; thiocyano groups; isothiocyano groups; azide groups; —$SO_2$ groups;

—OSO₃H groups; straight-chain, branched or cyclic alkyl, alkenyl or alkynyl groups; halogenated alkyl groups; hydroxyl groups; alkoxy groups; carboxylic acid and carboxylic ester groups; amine groups; carbamate groups, thiol groups, thioether and thioester groups; sulfoxide groups, sulfone groups; sulfide groups; sulfate and sulfate ester groups; sulfonate and sulfonate ester groups; sulfonamide groups, sulfonate ester groups; phosphine groups; phosphate and phosphate ester groups; phosphonate and phosphonate ester groups; and alkyl-substituted silyl groups.

In certain embodiments, the photolabile moiety has the chemical structure:

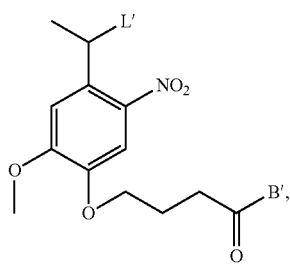

wherein L' is a covalent linkage to the first linking moiety, and wherein B' is a covalent linkage to the backbone structure.

In some embodiments, the backbone structure can be poly(ethylene glycol), poly(ethylene oxide), poly(vinyl alcohol), poly(styrene), poly(acrylate), poly(methacrylate), poly(vinylether), poly(urethane), polypropylene, polyester or polyethylene.

In some embodiments, the macromer has the chemical structure:

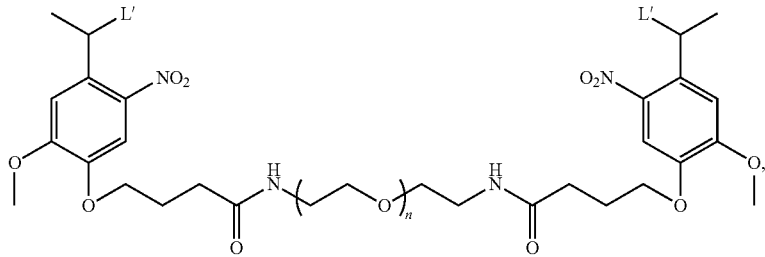

wherein L' is a covalently linkage to the first linking moiety.

In some such embodiments, the macromer has the chemical structure:

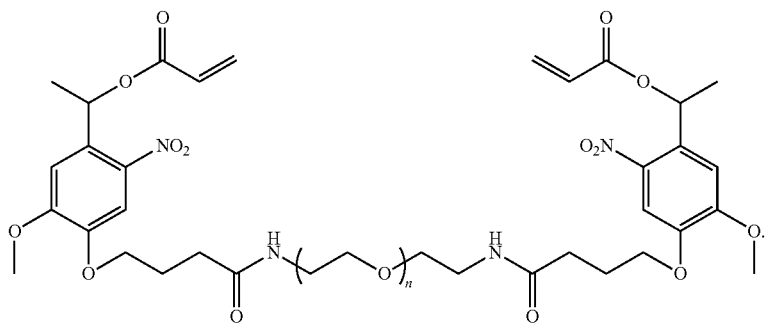

In some embodiments, the cell-binding moiety comprises a hapten-binding moiety. Optionally, the hapten-binding moiety may be a biotin-binding moiety, an apatamer-binding moiety, or a glycan-binding moiety. Optionally, the biotin-binding moiety may include avidin or NeutrAvidin.

In some embodiments, the cell-binding moiety is acrylated. In some embodiments, the cell-binding moiety may include a cell-binding agent, such as an antibody. The antibody may be biotinylated, and/or may be capable of binding to circulating tumor cells (CTC), such as prostate cancer cells (PC3) and lung cancer A549 cells. The antibody may be an anti-EpCAM antibody, and the CTC may be an EpCAM expressing cell.

In some embodiments, the photoinitiator is Lithium phenyl-2,4,6-trimethylbenzoylphosphinate (LAP).

In some embodiments, the light may be in the visible wavelength range.

In a third aspect, the disclosure encompasses a method of capturing one or more cells from a fluid. The method includes the steps of (a) preparing a photodegradable hydrogel as described above, and (b) contacting the hydrogel with a fluid comprising a biological sample that may contain one or more cells. The one or more cells are capable of being captured by the cell-binding moiety, and the cells are captured by the cell-binding moiety.

In some embodiments, the cell is a mammalian cell. In some embodiments, the cell is a cancer cell. In some such embodiments, the cell is a circulating tumor cell (CTC). Optionally, the CTC may be a prostate cancer cell (PC3) or a lung cancer A549 cell. Optionally, the CTC is an EpCAM-expressing cell.

In some embodiments, the step of contacting the hydrogel with a fluid comprising a biological sample takes place within a microfluidic device.

In a fourth aspect, the disclosure encompasses a method of selectively capturing and releasing one or more cells in a fluid. The method includes the steps of (a) preparing a photodegradable hydrogel as described previously; (b) contacting the hydrogel with a fluid comprising a biological sample that may contain one or more cells, wherein the one or more cells are capable of being captured by the cell-binding moiety; and (c) exposing the hydrogel to light, whereby the one or more cells are released from the hydrogel.

In some embodiments, the hydrogel is disposed on at least an interior surface of a microfluidic device, and the fluid is contacted with the hydrogel by being passed through the microfluidic device. In some such embodiments, the interior surface is further functionalized to facilitate a covalent linkage between the hydrogel and the surface. In some such embodiments, the interior surface is functionalized to be capable of linking to a CHxCHy moiety, wherein x is 0 or 1 and y is 1 or 2. The interior surface may be acrylated, by for example, being functionalized with an acrylated silane.

In some embodiments, the hydrogel is exposed to light within the microfluidic device.

Some embodiments further include the step of detecting the one or more cells released from the hydrogel.

In some embodiments, the cell is a mammalian cell. In some embodiments, the cell is a cancer cell. In some such embodiments, the cancer cell is a circulating tumor cell (CTC). Optionally, the CTC may be a prostate cancer cell (PC3) or a lung cancer A549 cell. Optionally, the CTC may be an EpCAM-expressing cell.

In certain embodiments, the light is in the UV light wavelength range.

In a fifth aspect, the disclosure encompasses a microfluidic device for assaying for the presence of cells in a fluid. The device includes (a) a micro-channel defined by at least three flat internal surfaces or one or more curved internal surfaces; and (b) a photodegradable as described previously, wherein the hydrogel is coated on at least one of the surfaces.

In some embodiments, the interior surface is further functionalized to facilitate a covalent linkage between the hydrogel and the surface. For example, the interior surface may be functionalized to be capable of linking to a CHxCHy moiety, wherein x is 0 or 1 and y is 1 or 2. In some such embodiments, the interior surface may be acrylated or functionalized with an acrylated silane.

In some embodiments, at least one micro-channel surface has three dimensional patterning. In some embodiments, at least one surface comprises poly(dimethylsiloxane) (PDMS). In some embodiments, at least one interior surface includes a groove.

In a sixth aspect, the disclosure encompasses a kit for capturing one or more cells in a fluid. The kit includes (a) a macromer having the chemical structure: L-P-B-P-L; wherein (i) L is a first linking moiety terminating with —CH$_x$CH$_y$, wherein the bond between the two carbon atoms is a covalent double or triple bond capable of taking part in an addition polymerization reaction, and wherein x is 0 or 1 and y is 1 or 2; (ii) P is a photolabile moiety; and (iii) B is a backbone structure comprising one or more repeating units that may be the same or different; (b) a cell-binding moiety attached to a second linking moiety terminating with (i) —CH$_x$CH$_y$, wherein the bond between the two carbon atoms is a covalent double or triple bond capable of taking part in an addition polymerization reaction, and wherein x is 0 or 1 and y is 1 or 2, or (ii) —SH, wherein —SH is capable of taking part in one or more chain-growth polymerization, step-growth polymerization, or mixed-mode polymerization; and (c) a photoinitiator capable of producing free radicals in the presence of light.

In some embodiments, the first linking moiety, the second linking moiety, or both include a terminal acrylate group.

In some embodiments, the photolabile moiety has the chemical structure:

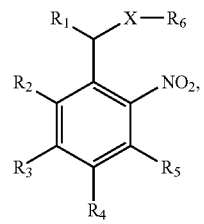

where X is O, N or S; $R_1$ is selected from the group consisting of: hydrogen, straight-chain or branched C1-C10 alkyl, aryl, alkoxy, aryloxy or carboxy groups in which one or more carbon atoms can be independently optionally substituted with one or more heteroatoms, and one or more hydrogen atoms can be independently optionally substituted with hydroxyl, halogen or oxygen atoms.

$R_2$-$R_6$ are independently selected from the group consisting of hydrogen; one or more polymerizable groups, one or more reactive end groups; straight chain, branched or cyclic C1-C20 alkyl, alkenyl, alkynyl groups in which one or more of the carbon atoms are optionally substituted with non-hydrogen substituents and wherein one or more C, CH or CH$_2$ moiety can be replaced with an oxygen atom, a nitrogen atom, an NR' group, or a S atom; and an optionally substituted aromatic or non-aromatic ring structure, wherein two or more R groups can be linked to form one or more rings which can contain one or more of the same or different heteroatoms.

One or more R groups can be optionally substituted with one or more substituent groups selected from halogens; nitro groups; cyano groups; isocyano groups; thiocyano groups; isothiocyano groups; azide groups; —SO$_2$ groups; —OSO$_3$H groups; one or more optionally substituted straight-chain, branched or cyclic alkyl, alkenyl or alkynyl groups; OR'; —CO—OR'; —O—CO—R'; —N(R')$_2$; —CO—N(R')$_2$; —NR'—CO—OR'; —SR'; —SOR'; —SO$_2$—R'; —SO$_3$R'; —SO$_2$N(R')$_2$; —P(R')$_2$; —OPO$_3$(R')$_2$; and —Si(R')$_3$ wherein each R', independent of other R' in the substituent group can be a hydrogen, an optionally substituted straight-chain, branched or cyclic alkyl, alkenyl or alkynyl group wherein one or more C, CH or CH$_2$ groups therein can be replaced with an O atom, N atom, S atom or —NH group; an optionally substituted aromatic group, two or more R' groups can be linked together to form a ring which may contain one or more of the same or different heteroatoms.

R' can in turn be optionally substituted with one or more groups selected from the group consisting of halogens, nitro groups; cyano groups; isocyano groups; thiocyano groups; isothiocyano groups; azide groups; —SO$_2$ groups; —OSO$_3$H groups; straight-chain, branched or cyclic alkyl, alkenyl or alkynyl groups; halogenated alkyl groups; hydroxyl groups; alkoxy groups; carboxylic acid and carboxylic ester groups; amine groups; carbamate groups, thiol groups, thioether and thioester groups; sulfoxide groups, sulfone groups; sulfide groups; sulfate and sulfate ester groups; sulfonate and sulfonate ester groups; sulfonamide groups, sulfonate ester groups; phosphine groups; phosphate and phosphate ester groups; phosphonate and phosphonate ester groups; and alkyl-substituted silyl groups.

In some embodiments, the photolabile moiety has the chemical structure:

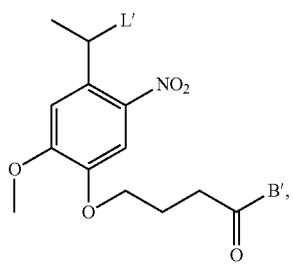

wherein L' is a covalent linkage to the first linking moiety, and wherein B' is a covalent linkage to the backbone structure.

In some embodiments, the backbone structure is selected from the group consisting of poly(ethylene glycol), poly(ethylene oxide), poly(vinyl alcohol), poly(styrene), poly(acrylate), poly(methacrylate), poly(vinylether), poly(urethane), polypropylene, polyester and polyethylene.

In some embodiments, the macromer has the chemical structure:

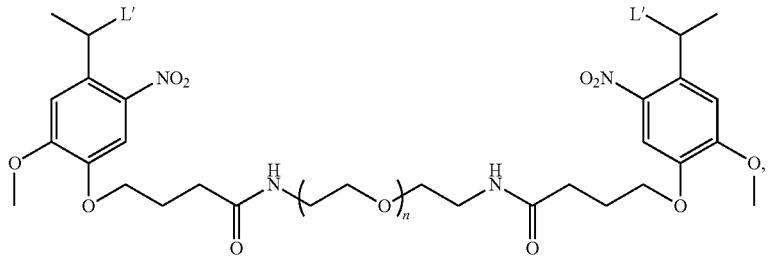

wherein L' is a covalently linkage to the first linking moiety. In some such embodiments, the macromer has the chemical structure:

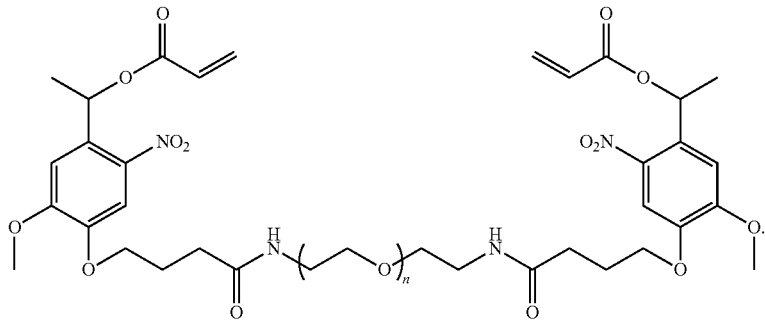

In some embodiments, the cell-binding moiety includes a hapten-binding moiety. Optionally, the hapten-binding moiety is a biotin-binding moiety, an aptamer-binding moiety or a glycan-binding moiety. Optionally, the biotin-binding moiety may include avidin or NeutrAvidin.

In some embodiments, the cell-binding moiety is acrylated. In some embodiments, the cell-binding moiety includes a cell-binding agent, such as an antibody. Optionally, the antibody may be biotinylated and/or may be capable of binding to circulating tumor cells (CTC), such as prostate cancer cells (PC3) or lung cancer A549 cells. In some embodiments, the antibody may be an anti-EpCAM antibody and the CTC may be an EpCAM expressing cell.

In some embodiments, the photoinitiator is lithium phenyl-2,4,6-trimethylbenzoylphosphinate (LAP).

In some embodiments, the kit further includes a microfluidic device.

Further objects, features and advantages of the invention will be apparent from the following detailed description when taken in conjunction with the accompanying drawings.

Figure 1:
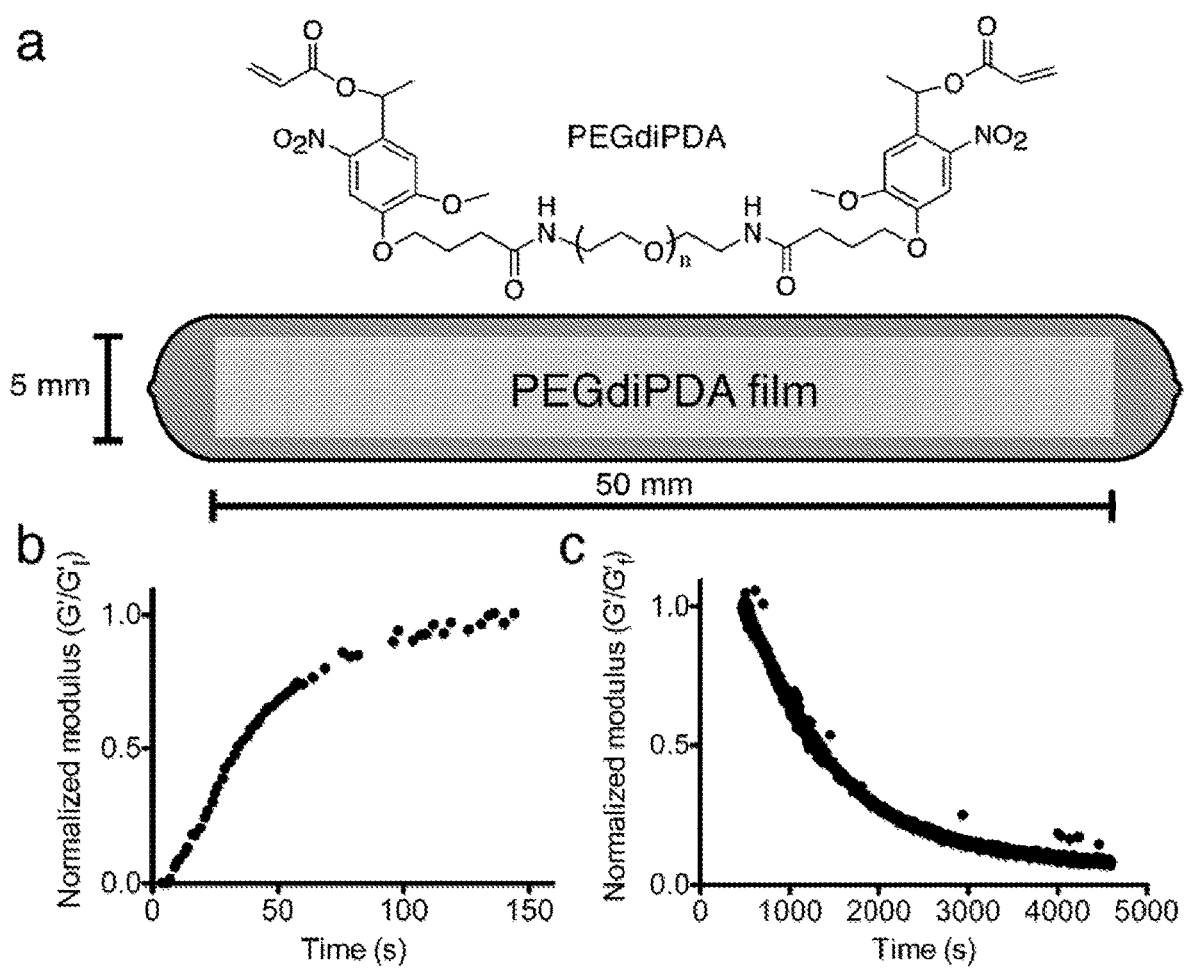
FIG. 1. Photopolymerization of PEGdiPDA hydrogels for microfluidic capture devices. (a) schematic diagram shows PEGdiPDA used in hydrogel formation and the hydrogel was formed on the surface of the microfluid device. (b) Graph of normalized modulus shows that PEGdiPDA hydrogels (13.2 wt % monomer; 3 wt % LAP) were photopolymerized with 2 min of visible light exposure ($\lambda$=400-500 nm; $I_0$=20 mW/cm$^2$) resulting in a final shear modulus G'=8200±200 Pa. (c) Graph of normalized modulus shows after complete polymerization, continued exposure of PEGdiPDA gels to light exposure ($\lambda$=400-500 nm; $I_0$=20 mW/cm$^2$) completely degraded the film over the course of an hour, demonstrated by the monotonic decrease in the normalized shear modulus.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DESCRIPTION OF THE INVENTION

In a first aspect, the present disclosure encompasses a photodegradable hydrogel for selectively capturing and releasing cells. As used herein the term "hydrogel" means a three-dimensional network of polymer chains, with water contained within the spaces in the network. The photodegradable hydrogel can be produced by the reaction of a macromer, a cell-binding moiety, and a photoinitiator upon exposure to light.

Macromer:

As used herein, a "macromer" is a group comprising one or more repeating units and one or more reactive end groups that can facilitate cross-linking with another group. For example, the macromer of the present disclosure has the chemical structure "L-P-B-P-L." L is a first linking moiety terminating with —CH$_x$CH$_y$, wherein the bond between the two carbon atoms is a covalent double or triple bond capable of taking part in an addition polymerization reaction, and wherein x is 0 or 1 and y is 1 or 2. L has a terminal structure comprising —CH=CH$_2$, —C≡CH, or the like. In a specific embodiment, L comprises the terminal moiety of —CH=CH$_2$. In another specific embodiment, L comprises a terminal acrylate group. In the presence of a photoinitiator, two of the first linking moieties of separate macromers cross-link through an addition polymerization reaction to form a hydrogel network.

P is a photolabile moiety. "Photolabile moiety" is a group containing one or more bonds that can be broken in response to exposure to radiation of the appropriate wavelength and energy. A broad range of wavelengths may be used for photodegradation. For example, wavelengths used may be in the ultraviolet spectrum, the visible spectrum, or the infrared spectrum, including without limitation UV-A (between about 320 and about 400 nm), UV-B (between about 280 and about 320 nm), and UV-C (between about 200 and about 280 nm). Other useful ranges include the wavelengths produced by visible, near-IR and IR lasers (about 500 nm to about 1.5 μm). A suitable or appropriate wavelength and energy can be readily determined by one of ordinary skill in the art by, for example, using an absorbance spectrum to determine what wavelength(s) will cause photodegradation.

In some embodiments, the photolabile moiety has the structure of

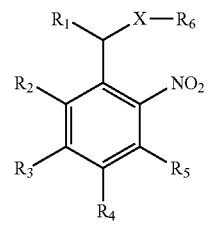

where X is O, N or S.

R$_1$ is selected from the group consisting of hydrogen, straight-chain or branched C$_1$-C$_{10}$ alkyl, aryl, 17xazolo, aryloxy or carboxy groups in which one or more carbon atoms can be independently optionally substituted with one or more heteroatoms, and one or more hydrogen atoms can be independently optionally substituted with hydroxyl, halogen or oxygen atoms. R$_2$-R$_6$ are independently selected from the group consisting of: hydrogen; one or more polymerizable groups, one or more reactive end groups; straight chain, branched or cyclic C$_1$-C$_{20}$ alkyl, alkenyl, alkynyl groups in which one or more of the carbon atoms are optionally substituted with non-hydrogen substituents and wherein one or more C, CH or CH$_2$ moiety can be replaced with an oxygen atom, a nitrogen atom, an NR' group, or a S atom; and an optionally substituted aromatic or non-aromatic ring structure, wherein two or more R groups can be linked to form one or more rings which can contain one or more of the same or different heteroatoms.

One or more R groups can be optionally substituted with one or more substituent groups selected from halogens; nitro groups; cyano groups; isocyano groups; thiocyano groups; isothiocyano groups; azide groups; —SO$_2$ groups; —OSO$_3$H groups; one or more optionally substituted straight-chain, branched or cyclic alkyl, alkenyl or alkynyl groups; OR'; —CO—OR'; —O—CO—R'; —N(R')$_2$; —CO—N(R')$_2$; —NR'—CO—OR'; —SR'; —SOR'; —SO$_2$—R'; —SO$_3$R'; —SO$_2$N(R')$_2$; —P(R')$_2$; —OPO$_3$(R')$_2$; and —Si(R')$_3$.

Each R', independent of other R' in the substituent group, can be a hydrogen, an optionally substituted straight-chain, branched or cyclic alkyl, alkenyl or alkynyl group wherein one or more C, CH or CH$_2$ groups therein can be replaced with an O atom, N atom, S atom or —NH group; or an optionally substituted aromatic group. Two or more R' groups can be linked together to form a ring which may contain one or more of the same or different heteroatoms; and R' can in turn be optionally substituted with one or more groups selected from the group consisting of halogens, nitro groups; cyano groups; isocyano groups; thiocyano groups; isothiocyano groups; azide groups; —SO₂ groups; —OSO₃H groups; straight-chain, branched or cyclic alkyl, alkenyl or alkynyl groups; halogenated alkyl groups; hydroxyl groups; carboxylic acid and carboxylic ester groups; amine groups; carbamate groups, thiol groups, thio-ether and thioester groups; sulfoxide groups, sulfone groups; sulfide groups; sulfate and sulfate ester groups; oxazolone and 18 oxazolone ester groups; sulfonamide groups; phosphine groups; phosphate and phosphate ester groups; and alkyl-substituted silyl groups. Any of the R groups may be linked to the backbone structure or the first linking moiety.

In some embodiments, the photolabile moiety has the chemical structure:

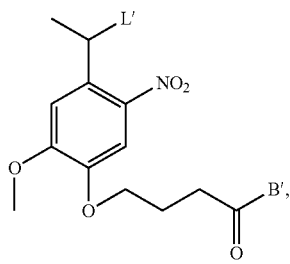

wherein L' is a covalent linkage to the first linking moiety, and wherein B' is a covalent linkage to the backbone structure.

glycol), poly(ethylene oxide), poly(vinyl alcohol), poly(vinylpyrrolidone), poly(ethyloxozoline), poly(ethylene oxide)/poly(propyleneoxide) block copolymers, polysaccharides, poly(hydroxylethylmethacrylates), poly(urethanes), poly(hydroxyethylacrylates), collagen, poly(ester)s, poly .alpha.-hydroxyesters, carbohydrates, proteins, poly (18xazolone), polyamino acids, poly(lactides), poly(styrenes), poly(acrylates), poly(methacrylates), poly(vinylethers), polyethylenes, poly(ethylene imine)s, polyesters, poly(urethane)s, and polypropylenes or any other polymer known in the art, and combinations thereof. Some backbones that are particularly useful for the present disclosure include poly(styrene), poly(acrylate), poly(methacrylate), poly(vinyl ether).

The backbone structure of the present disclosure can contain two or more different repeating units in any sequence, including random, gradient, alternating or block. The repeating units may also be amphiphilic with respect to each other, the photolabile moiety, the linking moiety and any other group in the macromer of the present disclosure.

The backbone structure connects to one or more photolabile moieties. In certain embodiments, the backbone structure is attached to two photolabile moieties, which may be the same or different.

One non-limiting example of the macromer is the chemical structure:

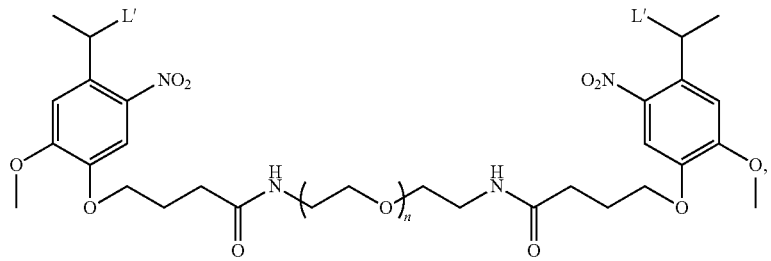

wherein L' is a covalent linkage to the first linking moiety.

In one such embodiment, the macromer has the chemical structure:

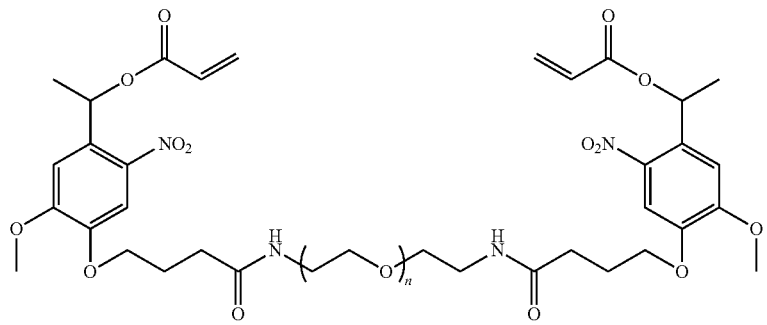

B is a backbone structure comprising one or more repeating units that may be the same or different. Generally, all repeating units that function in the macromers and polymers of the invention are intended to be included in this disclosure, even if not specifically mentioned. Examples of useful repeating units include, but are not limited to, poly(ethylene Cell-Binding Moiety:

The disclosed hydrogel also comprises a cell-biding moiety. This cell-binding moiety allows the hydrogel containing the macromer to selectively capture a cell. The cell-binding moiety comprises at least two functional end-groups, described as follows.

A first end-group of the cell-binding moiety is a second linking moiety capable of attaching to the first linking moiety of the macromer. The second linking moiety may have a terminal CHxHy group, wherein the bond between the two carbon atoms is covalent double or triple bond capable of taking part in an addition polymerization reaction, wherein x is 0 or 1 and y is 1 or 2. Thus, the CHxHy can be either —CH=CH$_2$ or —C≡CH. For this purpose, the cell-binding moiety is preferably acrylated.

The second linking moiety may also have a terminal —SH containing group (a thiolated group). During the formation of the hydrogel, the —SH can be covalently attached to the hydrogel by taking part in one or more of chain growth polymerization, step-growth polymerization, or mixed mode polymerization with the macromer.

A second end-group of the cell-binding moiety is capable of binding to a cell. The binding between the second end-group and cell can be direct or indirect. For binding directly to a cell, the second end-group itself comprises an active group capable of recognizing and capturing a cell. The active groups can be specifically selected to recognize and capture a specific cell type of interest, and cell recognition and capture can be accomplished by any means known in the art. For example, cell recognition can be based on chemical or biological reactions, including without limitation peptide recognition, nucleic acid recognition and/or chemical recognition. Cell recognition can also be based on non-chemical or non-biological reaction, such as, without limitations, electrokinetic recognition or size-dependent sorting.

To indirectly bind to a cell, the second end-group of the cell-binding moiety is attached to a cell through a separate cell-binding agent. Such cell-binding agents are well-known in the art.

The cell-binding agent may be a single component or be in a form of complex comprising two or more components, as long as at least one of the components is capable of binding to a target cell. For example, in addition to the component directly binding to a cell, the cell-binding agent or complex may comprise an additional component attached to the component binding to the cell.

In some embodiments, the cell-binding agent is a hapten-binding moiety. A "hapten" is a small molecule that can elicit an immune response only when attached to a large carrier, such as a protein. One example of a hapten-binding moiety is a biotin-binding moiety. As illustrated in the Example below, the biotin-binding moiety may comprise avidin or its analogs, which are capable of binding to a biotinylated cell-binding agent for a target cell. In some embodiments, the avidin may be in a deglycosylated form, such as NeutrAvidin.

Another example of a hapten-binding moiety is an aptamer-binding moiety. An aptamer is a nucleic acid sequence (typically DNA, RNA or related oligonucleotides) that can emerge from in vitro selections or other types of aptamer selection procedures well known in the art (e.g. bead-based selection with flow cytometry or high density aptamer arrays). Ligands that bind aptamers include but are not limited to small molecules, peptides, proteins, carbohydrates, hormones, sugars, metabolic byproducts, cofactors, drugs and toxins.

Aptamers configured to bind to specific target analytes can be selected by any means known in the art. For example, an apatamer can be selected by synthesizing an initial heterogeneous population of oligonucleotides, and then selecting oligonucleotides within the population that bind tightly to a particular target analyte. Once an aptamer that binds to a particular target molecule has been identified, it can be replicated using a variety of techniques known in biological and other arts, for example, by cloning and polymerase chain reaction (PCR) amplification followed by transcription.

Aptamers may further include suitable modifications that would allow the aptamer to be attached or bound to a cell. Suitable modifications include but are not limited to functional groups such as thiols, amines, carboxylic acids, maleimide, and dienes. Other methods such as hapten and biotin interactions may be used. Non-limiting examples of hapten or biotin interactions include strepatavidin-biotin pairing, x-biotin-biotin pairing, x-fluorescein/fluorescein pairing and other hapten or biotin pairings well known in the art.

Another example of the hapten-binding moiety is a glycan cell-binding moiety, which is capable of selectively binding to a glycan that is present on the exterior surface of a cell. As known in the art, "glycans" are sugars. Glycans can be monomers or polymers of sugar residues, but typically contain at lease three sugar which can be linear or branched. A glycan may include natural sugar residues (e.g., glucose, N-acetylglucosamine, N-acetyl neuraminic acid, galactose, mannose, fucose, hexose, arabinose, ribose, xylose, etc.) and/or modified sugars (e.g., 2'-fluororibose, 2'-deoxyribose, phosphomannose, 6'sulfo n-acetylglucosamine, etc). A glycan may include homo and heteropolymers of sugar residues. A glycan may also be a glycan component of a glycoconjugate (e.g., of a glycoprotein, glycolipid, proteoglycan, etc.), or may be a free glycan which has been cleaved or otherwise released from a glycoconjugate.

In one embodiment, the cell-binding agent, or one component of the cell-binding agent complex, can be antibodies, lymphokines, hormones, growth factors, vitamins, nutrient-transport molecules (such as transferrin), or any other cell-binding molecule or substance that specifically binds a target cell. When antibodies are used, they may optionally be monoclonal antibodies.

More specific non-limiting examples of cell-binding agents that can be used include:
(1) polyclonal and monoclonal antibodies, including fully human antibodies;
(2) single chain antibodies (polyclonal and monoclonal);
(3) fragments of antibodies (polyclonal and monoclonal) such as Fab, Fab', F(ab')$_2$, and Fv;
(4) chimeric antibodies and antigen-binding fragments thereof;
(5) domain antibodies (dAbs) and antigen-binding fragments thereof, including camelid antibodies;
(6) shark antibodies called new antigen receptors (Ig-NAR);
(7) interferons (e.g. alpha, beta, gamma);
(8) lymphokines such as IL-2, IL-3, IL-4, IL-6;
(9) hormones such as insulin, TRH (thyrotropin releasing hormone), MSH (melanocyte-stimulating hormone), steroid hormones, such as androgens and estrogens;
(10) growth factors and colony-stimulating factors such as EGF, TGF-alpha, FGF, VEGF, G-CSF, M-CSF and GM-CSF;
(11) transferrin; and
(12) vitamins, such as folate.

Particularly, monoclonal antibody techniques allow for the production of specific cell-binding agents in the form of monoclonal antibodies. Techniques for creating monoclonal antibodies are well known in the art. Such antibodies can be produced by, for example, immunizing mice, rats, hamsters or any other mammal with the antigen of interest. Antigens of interest may include the intact target cell, antigens isolated from the target cell, whole virus, attenuated whole virus, or viral proteins such as viral coat proteins. Sensitized human cells can also be used. Another method of creating monoclonal antibodies is the use of phage libraries of scFv (single chain variable region), specifically human scFv.

Selection of the appropriate cell-binding agent is a matter of choice that depends upon the particular cell population that is to be targeted. For example, the cell to be targeted can be any type of cells known in the art. It can be a cancer cell, stem cell, fetal cell, a viral-, a bacterial-, or a fungal-infected cell.

In one embodiment, the target cells of the present disclosure are cancer cells. The cancer cell can be a cell from any type of cancer, such as an epithelial cancer, including, but not limited to, breast cancer cells, prostate cancer cells, colorectal cancer cells, lung cancer cells, pancreatic cancer cells, ovarian cancer cells, bladder cancer cells endometrial or uterine cancer cells, cervical cancer cells, liver cancer cells, renal or kidney cancer cells, thyroid cancer, bone cancer cells, lymphoma cells, melanoma cells, and non-melanoma skin cancer cells.

In some specific embodiments, the target cancer cells are circulating tumor cells (CTCs). As well-known in the art, CTCs are cells that have detached from a primary tumor and circulate in the bloodstream. CTCs may constitute seeds for subsequent growth of additional tumors (metastasis) in different tissues, such as, but not limited to, lung, breast and colon. Thus, detection of CTCs can provide for diagnosis and/or prognosis for overall survival and therapeutic implications in subjects with cancers such as metastatic prostate and breast cancer. The number of CTCs in any patient sample (e.g., a blood sample) can be very small, which can make detection difficult. For example, because epithelial cell adhesion molecule (EpCAM) is a biomarker associated with epithelial cells, a CTC detection can be based on the detection of EpCAM expression.

For example, where the target cell is a breast cancer cell, the cell-binding agent, or one component of the cell-binding agent complex, may be an antibody that specifically binds to EpCAM (epithelial cell adhesion molecule), Her2/neu (Human Epidermal growth factor Receptor 2), MUC-I. EGFR (epidermal growth factor receptor), TAG-12 (tumor associated glycoprotein 12), IGF1-R (insulin-like growth factor 1 receptor), TACSTD2 (tumor associated calcium signal transducer 2), CD318, CD340, CD104, N-cadherin or a combination of two or more thereof, Where the target cell is a prostate cancer cell, the cell-binding agent, or one component of the cell-binding agent complex, may be antibody that specifically binds to EpCAM, MUC-I, EGFR, PSMA (prostate specific membrane antigen), PSA (prostate specific antigen), TACSTD2, PSCA (prostate stem cell antigen), PCSA (prostate cell surface antigen), CD318, CD 104, N-cadherin or a combination thereof, In another embodiment, the target cell is a colorectal cancer cell and the first binding entity is an antibody that specifically binds to EpCAM, CD66c, CD66e, CEA (carcinoembryonic antigen), TACSTD2, CK20 (cytokeratin 20). CDl 04, MUC-I, CD31-S, N-cadherin or a combination thereof.

Where the target cell is a lung cancer cell, the cell-binding agent, or one component of the cell-binding agent complex, may be an antibody that specifically binds to CKlS. CK19. CEA, EGFR, TACSTD2, CD318, CD104, or EpCAM or a combination thereof. Examples of target lung cancer cells include, but are not limited to A549 cells (non-small cell lung cancer-derived), Lu-141 cells (small cell carcinoma origin), PC-14 cells (adenocarcinoma origin), and the like.

Where the target cell is a pancreatic cancer cell, the cell-binding agent, or one component of the cell-binding agent complex, may be an antibody that specifically binds to MUC-I, TACSTD2, CEA. CD104. CD318, N-cadherin, EpCAM or a combination thereof, Where the target cell is an ovarian cancer cell, the cell-binding agent, or one component of the cell-binding agent complex, may be an antibody that specifically binds to MUC-I, TACSTD2, CD318, CD104, N-cadherin, EpCAM or a combination thereof.

Where the target cell is an endothelial bladder cancer cell, the cell-binding agent, or one component of the cell-binding agent complex, can be an antibody that specifically binds to CD34, CD146, CD62, CD105, CD 106, VEGF receptor (vascular endothelial growth factor receptor), MUC-I or a combination thereof. Or where the target cell is an epithelial bladder cancer cell, the cell-binding agent is an antibody that specifically binds to TACSTD2. EpCAM, CD318, EGFR, 6B5 or Folate binding receptor, Where the target cell is a cancer stem cell, the cell-binding agent, or one component of the cell-binding agent complex, may be an antibody that specifically binds to CD133, CD135, CD 117, CD34 or a combination thereof.

Where the target cell is a circulating cancer cell that expresses mesenchymal antigens, the cell-binding agent can be an antibody (or antibody cocktail) that specifically binds to FGFR1, FGFR4, EGFR, N-cadherin, folate binding receptor, and MSC or a combination thereof.

Where the target cell is a circulating cancer cell that expresses angiogenesis surface antigens, the cell-binding agent, or one component of the cell-binding agent complex, may be an antibody that specifically binds to a VEGF receptor.

Where the target cell is a melanoma cancer cell, the cell-binding agent, or one component of the cell-binding agent complex, may be an antibody that specifically binds to one or more of the melanocyte differentiation antigens, oncofetal antigens, tumor specific antigens, SEREX antigens or a combination thereof. Examples of melanocyte differentiation antigens, include but are not limited to tyrosinase, gp75, gplOO, M elan A/MART 1 or TRP-2. Examples of oncofetal antigens include antigens in the MAGE family (MAGE-A1, MAGE-A4), BAGE family, GAGE family or NY-ESO1. Examples of tumor-specific antigens include CDK4 and β-calenin. Examples of SEREX antigens include D-I and SSX-2.

For the purpose of this disclosure, the cell-binding agent can also be a combination of two or more different kind antibodies. For example, the antibody mixtures may comprise at least antibody against an epithelial cell surface antigen, and at least one antibody against an antigen that is indicative of a mesenchymal phenotype, to thereby the target cells having a range of epithelial and/or mesenchymal characteristics from the sample.

In a specific embodiment, the antibody is anti-EpCAM, which specifically binds to EpCAM expressing cancer cells in the sample.

Non-antibody molecules can also be used to target specific cancer cell populations. For example, GM-CSF, which binds to myeloid cells, can be used as a cell-binding agent to target diseased cells from acute myelogenous leukemia. In addition, IL-2, can be used to bind activated T-cells. MSH can be used to bind melanocytes. Folic acid can be used to target the folate receptor expressed on ovarian and other tumors. Epidermal growth factor (EGF) can be used to target squamous cancers such as lung and head and neck. Somatostatin can be used to target neuroblastomas and other tumor types. Cancers of the breast and testes can be successfully targeted with estrogen (or estrogen analogues) or androgen (or androgen analogues) respectively.

Photoinitiator:

As used herein, the term "initiator" refers to a substance introduced into a reaction system in order to bring about reaction or process generating free radicals or some other reactive reaction intermediates which then induce a chain reaction, preferably a chain reaction polymerization. The term "photoinitiator" in turn refers to a substance capable of initiating a chemical reaction, such as a polymerization of a monomer, when exposed to a light.

Many suitable photoinitiators will be known to one skilled in the art. Exemplary photoinitiators include, without limitation, Lithium phenyl-2,4,6-trimethylbenzoylphosphinate (LAP), bis(2,4,6-trimethylbenzoyl) phenylphosphine oxide (BAPO), 2,2-dimethoxy-2-phenylaceto-phenone (DMPA), camphorquinone (CQ), 1-phenyl-1,2-propanedione (PPD), the organometallic complex Cp'Pt(CH(3))(3) (Cp$^1$=eta(5)-C(5)H(4)CH(3)), 2-hydroxy-1-[4-(hydroxyethoxy)phenyl]-2-methyl-1-propanone (e.g., Irgacure™ 2959), dimethylaminoethyl methacrylate (DMAEMA), 2,2-dimethoxy-2-phenylaceto-phenone, benzophenone (BP), and flavins. In a preferred embodiment, the photoinitiator is LAP.

Formation and Degradation of Hydrogel:

The general procedure used to form or degrade the hydrogel is described in U.S. Pat. No. 8,343,710, which is incorporated herein by reference in its entirety.

Specifically in this case, when exposed to a light, the photoinitiator described herein is capable of producing free radicals. The free radicals produced may initiate an addition polymerization reaction, whereby the first linking moiety of the L groups of the macromer and the second linking moiety of the cell-binding moiety are incorporated into polymer chains, and the macromer is cross-linked to form a hydrogel. The cell-binding moiety is thereby incorporated into the hydrogel.

In some specific embodiments, the cell-binding moiety comprises a biotin-binding moiety at the second end-group of the cell-binding moiety. During hydrogel formation, the biotin-binding moiety can be covalently incorporated into the hydrogel network through interaction between the first linking moiety of the macromer and the first end-group (the second linking moiety) of the cell-binding moiety. Once the biotin-binding moiety is incorporated into the hydrogel, the biotin-binding moiety at the second end of the cell-binding moiety is capable of facilitating subsequent reaction or attachment to a cell-binding agent.

While a broad range of wavelength can be used for formation or degradation, a wavelength in the range between long UV to visible light is preferred in biological applications like capturing cells. In a specific example described below, the hydrogel is formed in the present of a visible light, and degraded in the present of a UV light.

In a second aspect, the present disclosure provides a method of capturing one or more cells in a fluid, the method comprising the steps of (a) preparing a photodegradable hydrogel comprising a cell-binding agent disclosed above; and (b) contacting the hydrogel with a fluid comprising a biological sample that may contain one or more cells, wherein the one or more cells are capable of being captured by the cell-binding moiety. The method may optionally include the step of determining whether one or more cells are captured on the hydrogel.

Subsequent action or analysis of the captured cells may be desired. For example, captured cells can be selectively released from the photodegradable hydrogel. Thus, in its third aspect, the present disclosure provides a method of assaying for the presence of cells or releasing cells, the method comprising the steps of (a) preparing a photodegradable hydrogel comprising a cell-binding agent disclosed above; (b) contacting the hydrogel with a fluid comprising a biological sample that may contain one or more cells, wherein the one or more cells are capable of being captured by the cell-binding moiety; (c) exposing the hydrogel to a light; and optionally (d) detecting whether one or more cells are released from the hydrogel. Preferably, the light for releasing is an ultraviolet light. Optionally, the light can be directed at a single area of the hydrogel. In some such embodiments, the light may be directed at an area containing a single captured cell, to facilitate the selective release of a single cell.

Detecting the presence of captured cells on the hydrogel can be by one of several methods known to those skilled in the art. For example, captured cells can be observed using a photomicroscope. Cells may also be detected by fluorescent or luminescent labeling.

As used herein, a "biological sample" is used in its broadest sense and includes liquid or nonliquid samples from a wide variety of sources. Examples of biological samples include, but are not limited to, tissue scrapings, whole blood, urine, cervical secretions, bronchial aspirates (including bronchial washings), sputum, saliva, feces, serum, synovial and cerebrospinal fluid, as well as laboratory preparations such as purified or partially purified macromolecules and cell culture materials. The sample may comprise at least one target cell.

In a fourth aspect, the present disclosure provides a microfluidic device for assaying for the presence of cells. The device includes (a) a micro-channel defined by at least three flat surfaces or by a curved surface; and (b) a photodegradable hydrogel described herein, wherein the hydrogel is coated on the surface of the micro-channel.

In some embodiments, the micro-channel is as described in U.S. Patent Application Publication No. 2011/0294187, which is incorporated herein by reference in its entirety. Specifically, the channel can be defined with three dimensional (3D) patterns. This 3D patterning allows one to affect the flow profile within the microchannel, which in turn enhances the interaction between the flowing sample solution and the capture surface, and subsequently significantly increases the cell capture efficiency. In some embodiments, the micro-channel surface is made from poly(dimethylsiloxane) (PDMS).

At least one interior surface of the micro-channel may further be functionalized to facilitate the subsequent binding between the surface and the hydrogel. Such functionalization can be achieved by any means known in the art. As a non-limiting example, the surface of the micro-channel can be functionalized with an acrylated silane to enable covalent attachment between the CHxCHy moieties of the macromer of the hydrogel and the acrylated groups of the micro-channel surface.

In a fifth aspect, the present disclosure provides a kit for assaying for the presence of cells in a fluid. The kit comprises (a) a macromer as described herein; (b) a cell-binding moiety as described herein; and (c) a photoinitiator as described herein. The kit may further comprise a microfluidic device as described herein.

The following example is offered for illustrative purposes only, and is not intended to limit the scope of the invention in any way. Indeed, various modifications of the invention in addition to those shown and described herein will become apparent to those skilled in the art from the foregoing description and the following example and fall within the scope of the appended claims.

Example

Materials and Methods

All reagents were purchased from Sigma Aldrich except as otherwise noted.

Hydrogel Precursor Synthesis.

Poly(ethylene glycol) diphotodegradable acrylate (PEG-diPDA) was synthesized as previously described.[14] Lithium phenyl-2,4,6-trimethylbenzoylphosphinate (LAP) was synthesized as previously described.[15] Acrylated NeutrAvidin was synthesized based on a previously published acrylation procedure.[16] Briefly, NeutrAvidin (Life Technologies) was acrylated by reacting the NeutrAvidin (2 mg/mL) with 3400 Da Acryl-PEG-NHS (Laysan Bio) at a 1:40 molar ratio, respectively, in 50 mM sodium bicarbonate buffer, pH 8.4. The reaction proceeded for 4 h at room temperature under constant rocking. Unreacted Acryl-PEG-NHS was removed by passing the solution through a Zeba Spin Desalting Column (7K MWCO; Thermo Scientific), and the solution was lyophilized to recovered acrylated-NeutrAvidin (AcrylNA). AcrylNA was resuspended at 10 mg/mL in PBS after lyophilization.

PEGdiPDA Hydrogel Fabrication.

Stock solutions of PEGdiPDA (20 wt % in PBS), poly(ethylene glycol) monoacrylate (PEGA, $M_n$~400 Da; 40 wt % in PBS; Monomer-Polymer and Dajac Labs), LAP (8 wt % in PBS), and AcrylNA (10 mg/mL in PBS) were prepared. The gel forming monomer solution (13.2 wt % monomer) was formulated with PEGdiPDA (8.2 wt %), PEGA (5 wt %), LAP (3 wt %), and AcrylNA (0.9 mg/mL), and the solution was mixed with a vortex. PEGdiPDA hydrogels were photopolymerized using collimated visible light ($\lambda$=400-500 nm; $I_0$~20 mW/cm$^2$; EFOS Novacure with liquid light guide and collimating lens). The gels were polymerized for 2 min to minimize cleavage of the o-nitrobenzyl ether groups in the PEGdiPDA at the photoinitiating wavelengths.

Hydrogel Fabrication in Microfluidic Devices.

Clean glass slides were functionalized with an acrylated silane to enable covalent attachment between the PEGdiPDA hydrogel and the glass surface. To acrylate the glass slides, they were submerged in a mixture of 30 mL ethanol (95% in DIH$_2$O), acetic acid (enough to lower the solution pH to 4.5-5.5), and 170 µL (3-Acryloxypropyl)trimethoxy silane (APTS). Poly(dimethylsiloxane) (PDMS) channels were placed on top of the cleaned glass slides, and the location of the channel was marked to allow for future alignment of microfluidic channels over the formed gels. The microfluidic channel was then filled with the APTS solution, which was allowed to react with the glass for ~3 min. The APTS solution was then flushed out of the channel, the glass slide was rinsed in ethanol (95% in DIH$_2$O); and the prepared slides were placed in an oven (80° C.) for ~15 min. Fresh microfluidic channels were placed over the silanized region of the glass slide, filled with the PEGdiPDA gel precursor solution (~10 µL), and quickly placed under the collimated visible light to polymerize the gel for 2 min. The microfluidic channels were removed, and PEGdiPDA gels attached to glass slides were immersed in PBS overnight prior to use.

Fabrication of Multifaceted PEGdiPDA Hydrogels.

Multifaceted gels were created as described above, except that the AcrylNA was replaced with BSA-Alexa Fluor 488 (BSA-488) or BSA-Alexa Fluor 594 (BSA-594), final concentration of 0.45 mg/mL. Dual-inlet microfluidic channels were placed over silanized glass slides with each inlet reserved for either the BSA-488 or the BSA-594 PEGdiPDA gel precursor solutions. The channels were filled with a glycerol solution (40 v % in DIH$_2$O). Once the channel was completely filled with the glycerol solution, the two labeled PEGdiPDA precursor solutions were loaded into the device through the microfluidic channel. After the channel was filled with the two solutions, the gel was polymerized for 2 min; the microfluidic channel was removed; and the gels were immersed in PBS overnight prior to imaging. Multifaceted PEGdiPDA films were imaged on an upright confocal laser scanning microscope (Zeiss LSM 710 NLO).

PEGdiPDA Hydrogel Functionalization.

PEGdiPDA gels were formed as described above with varying concentrations of AcrylNA (0 mg/mL to 0.9 mg/mL). Circular gaskets (~0.5 mm in height) with a diameter of ~1 cm were used to form the gels. The gels were rinsed in PBS for 1 h and then blocked in a 3% BSA solution in PBS for 1 h. After blocking, the gels were exposed to a biotinylated fluorescein (Life Technologies) for 1 h. Gels were then rinsed with PBS overnight to remove any unreacted biotinylated fluorescein. The gels were imaged with an upright confocal laser scanning microscope (Zeiss LSM 710 NLO) to monitor the fluorescein intensity, which was quantified with ImageJ (NIH). For cell capture experiments, PEGdiPDA gels with 0.9 mg/mL AcrylNA were functionalized with a biotinylated anti-EpCAM antibody (R&D Systems BAF960, 20 µg/mL in 1% BSA) to capture EpCAM expressing cells.

Cell Culture, Capture, and Release.

PC3 prostate cancer (ATCC) cells were cultured in F-12K medium with 10% FBS at 37° C. and 5% CO$_2$. Static cell capture experiments were conducted by seeding PC3 cells on anti-EpCAM functionalized and blank PEGdiPDA gels. For the flow capture experiments, PBS spiked with PC3s ($1\times10^6$ cells/mL) was flowed (2 l/min) through a microfluidic channel over an anti-EpCAM functionalized PEGdiPDA thin film. After the cells were flowed over the PEGdiPDA gel, the device was rinsed with 10× volumes of PBS (20 µL/min). For release, cell capture devices were placed on an inverted epifluorescent microscope (Nikon TE 2000), and regions of the gel were exposed to UV light using the DAPI filter cube ($\lambda$~350-370 nm) under flow (1 µL/min). The devices were imaged during light exposure to monitor degradation-induced cell release.

Results and Discussion

Photopolymerization of PEGdiPDA Films.

Figure 4:
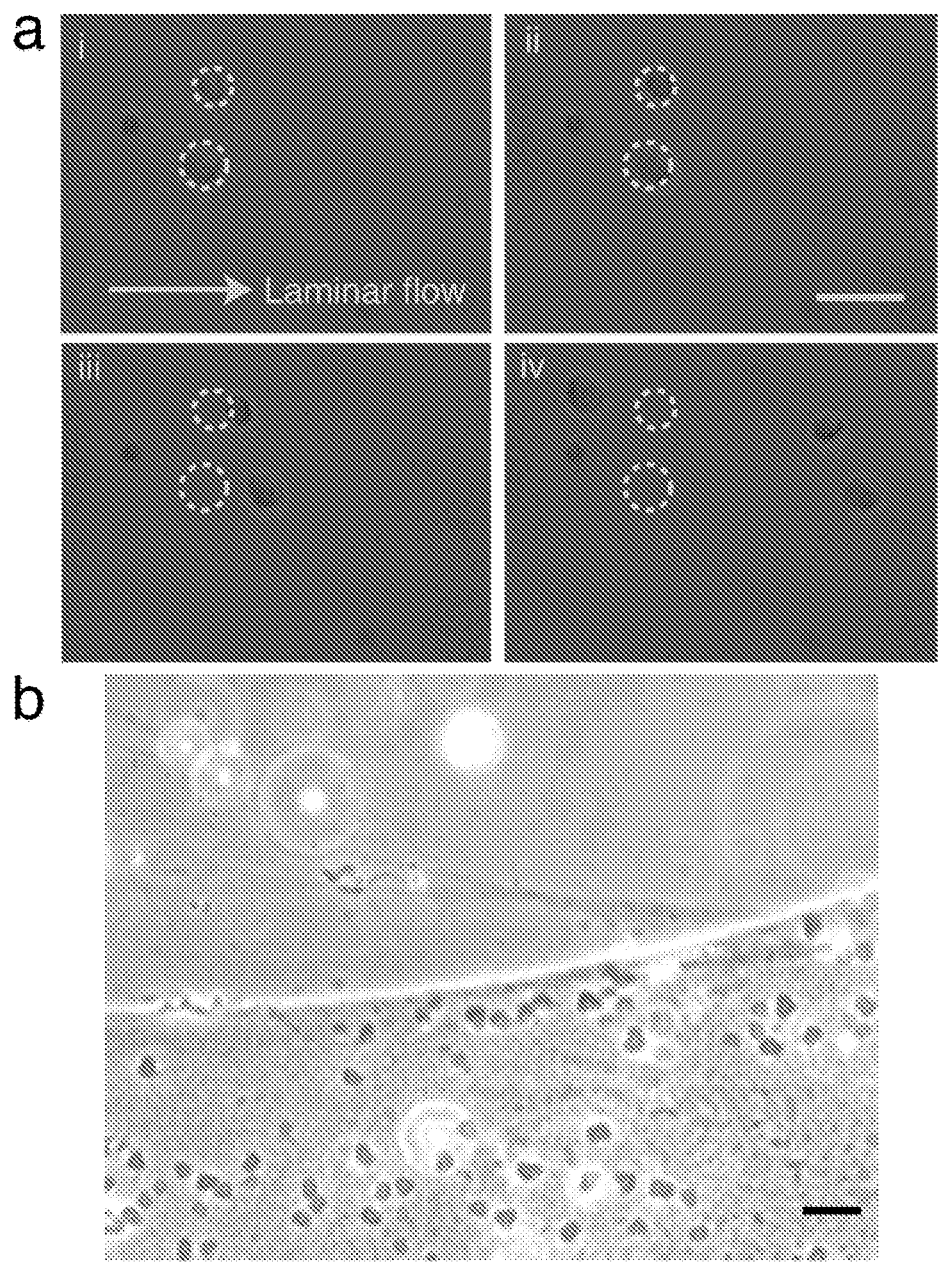
FIG. 4. Microscopic photos of cell capture and release with PEGdiPDA microfluidic devices. (a) Photos show capture and release of PC3 prostate cancer cells. The cells expressing EpCAM were captured with anti-EpCAM functionalized PEGdiPDA hydrogels under continuous flow (i). UV light (λ=350-370 nm) was employed to degrade the thin film selectively under specific cells to release them from the capture surface. Cells initially began to release from the capture location (ii), then began to roll away in the direction of continuous flow (iii), and finally became entrained in the flow for full release (iv). (b) Photo shows that PC3 cells were completely released in regions of degradation, curved feature on the top of the picture, but remained attached to the non-degraded regions of the film. Scale bars, 60 m.

A photolabile, macromolecular monomer, poly(ethylene glycol) diphotodegradable acrylate (PEGdiPDA)[14,17] was employed to fabricate photopolymerized, photodegradable hydrogels (FIG. 1a). Lithium phenyl-2,4,6-trimethylbenzoylphosphinate (LAP)[CITE Fairbanks Biomaterials] enabled visible light ($\lambda$=400-500 nm; $I_0$=20 mW/cm$^2$) initiation of polymerization with minimal cleavage of the photolabile o-nitrobenzyl ether (NBE) moieties (FIG. 1b) owing to the differences in quantum yield and molar absorptivity between LAP and NBE.[15,18] Complete polymerization as assessed by in situ rheometry (G'=8200±200 Pa) occurred in ~2 min, during which time the concentration of photolabile NBE moieties remained at ~90% of its initial concentration.[18] Upon photopolymerization with LAP, PEGdiPDA hydrogels were still able to degrade completely, as demonstrated by monitoring the shear modulus decrease during continued irradiation with visible light (FIG. 1c; $\lambda$=400-500 nm). Similarly, UV light exposure from an inverted epifluorescent microscope (λ=350-370 nm; Nikon TE2000 FS) rapidly eroded regions of the PEGdiPDA films (FIG. 4b).

Functionalizing Gels with Biotinylated Molecules.

Figure 2:
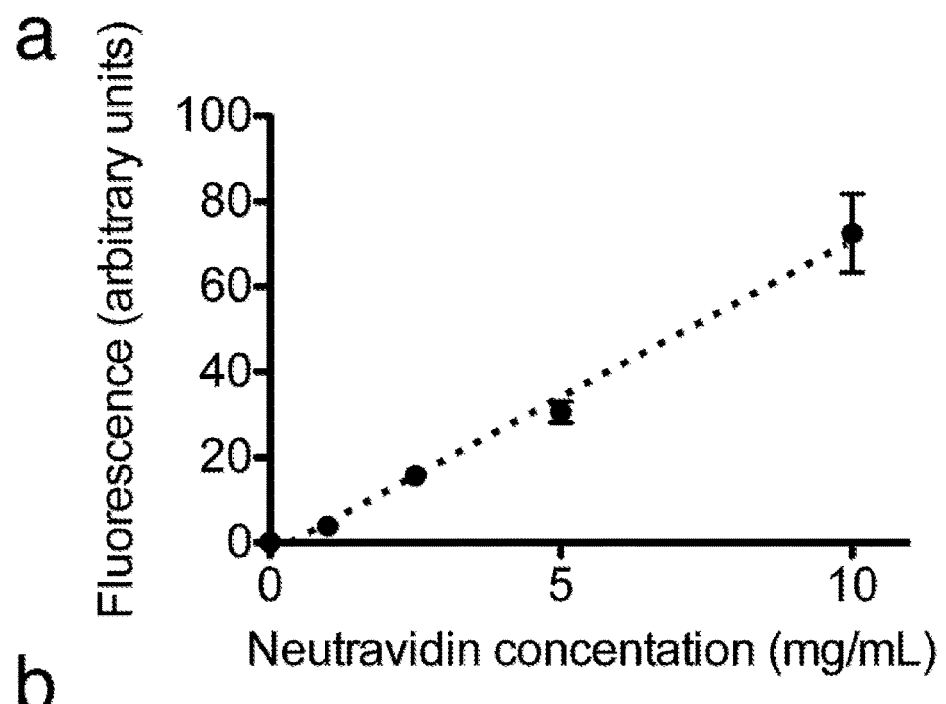
FIG. 2. Observed fluorescence on a functionalized PEGdiPDA hydrogel films. (a) Graph of fluorescence indicates that Acrylated-NeutrAvidin (AcrylNA) was incorporated into PEGdiPDA hydrogels at a range of concentrations (0 to 0.9 mg/mL). Biotinylated-fluorescein was coupled to the available AcrylNA in the gels, and the incorporation of NeutrAviding led to a dose-dependent increase in biotin binding. This demonstrates that a range of concentrations in surface functionality can be presented using AcrylNA into PEGdiPDA hydrogels. (b) Photographs showing capture of EpCAM cancer cells on the hydrogels. PEGdiPDA hydrogels were also functionalized with a cell capture antibody (biotinylated anti-EpCAM), and EpCAM expressing cancer cells (1×10$^6$ cells/mL) were only captured on anti-EpCAM functionalized gels in static capture experiments. Scale bars, 100 μm.
Figure 2:
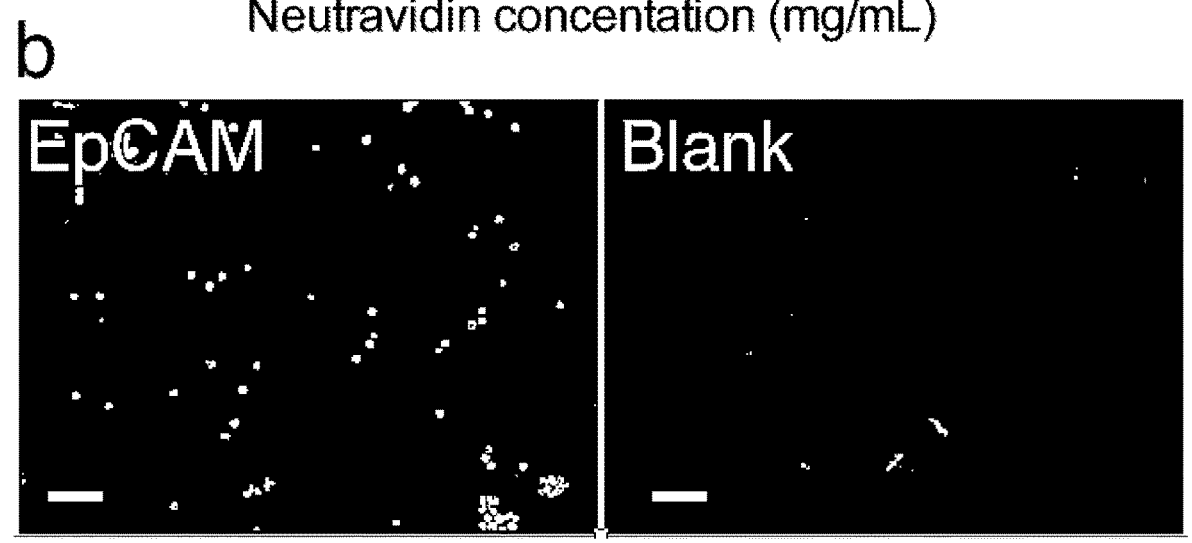

Reactive NeutrAvidin groups were covalently incorporated into PEGdiPDA hydrogel films to facilitate subsequent functionalization with biotinylated molecules. Acrylated-NeutrAvidin (AcrylNA) was included in the hydrogel precursor solution so that the pendant acrylate group would react with growing kinetic chains during network formation. To monitor the incorporation of AcrylNA into PEGdiPDA films, films with a range of AcrylNA concentrations in the precursor solution were exposed to a biotinylated probe (Biotin-fluorescein; Life Technologies). Confocal microscopy confirmed that the biotinylated fluorophore reacted with and became bound to AcrylNA functionalized gels in a dose-dependent manner (FIG. 2a). The level of incorporation of AcrylNA into the precursor solution can control the degree of functionalization, but high-affinity capture devices (10 mg/mL AcrylNA) were used for the cell capture experiments. For static cell culture experiments, PEGdiPDA gels were functionalized with biotinylated anti-EpCAM. These experiments confirmed the bioavailability of functional molecules incorporated into the gels, as EpCAM expressing cancer cells adhered to anti-EpCAM functionalized gels and not to control, blank gels (FIG. 2b).

Multifaceted Capture Devices.

Figure 3:
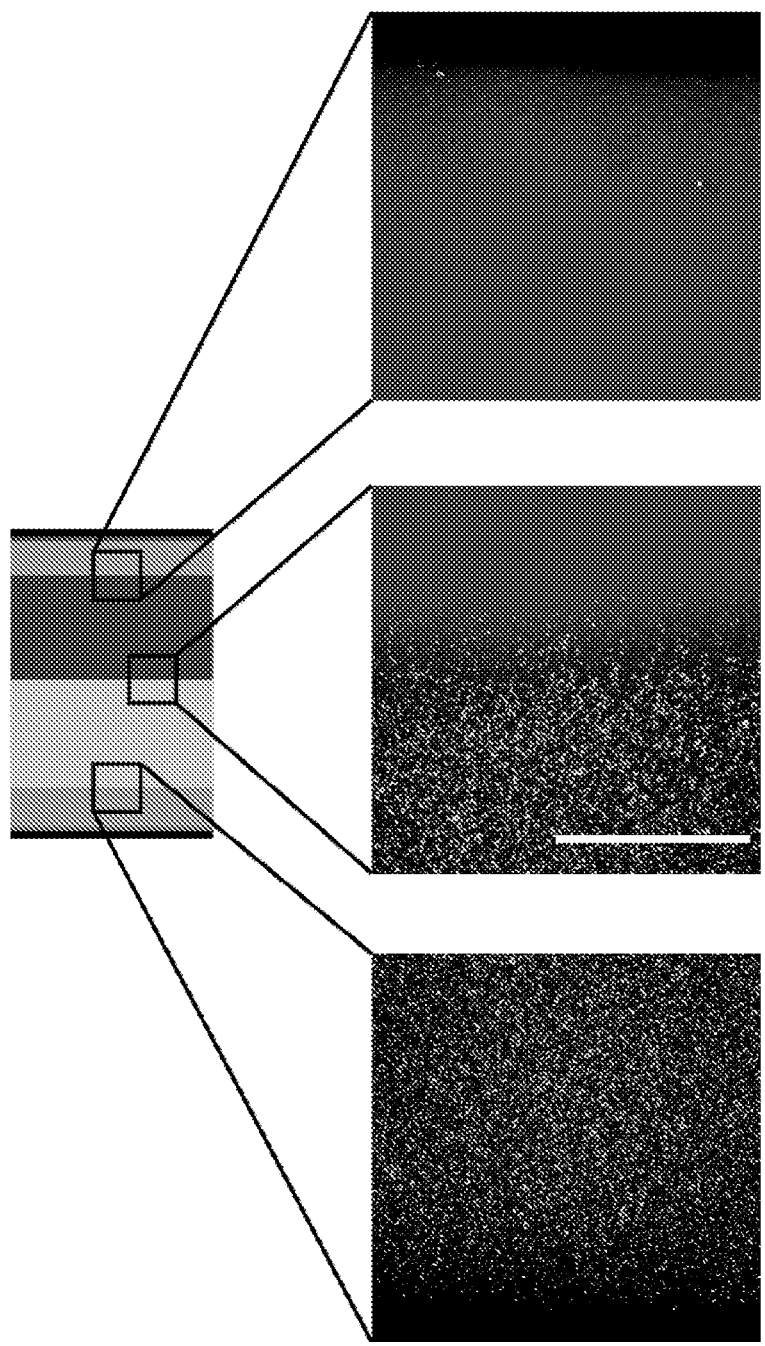
FIG. 3. Schematic diagrams and photographs of multifaceted hydrogels on the surface of the microfluid devices. Dual-layer PEGdiPDA hydrogels were photopolymerized into the microfluidic channels functionalized with BSA-488 (green) and BSA-594 (red), demonstrating the ability to present multiple, disparate surfaces to a cell suspension during flow. In this manner, the ability to spatially capture separate populations of cells from a single cell suspension could be realized. Scale bar, 400 μm.

Current microfluidic capture devices have demonstrated the efficient capture of single cell subtypes;[2,3,6,10] however, it would be beneficial to capture multiple cell populations within a single device and recover them sequentially for cell purification or increased capture throughput. Multifaceted PEGdiPDA hydrogels were fabricated to demonstrate that the use of photopolymerization within microfluidic devices enables the facile generation of multifaceted devices. Two precursor solutions (PEGdiPDA with BSA-488 and PEG-diPDA with BSA-594) were drawn into a two-inlet microfluidic device to create side-by-side PEGdiPDA gels (FIG. 3). There was minimal mixing (~100 m) at the interface of the two solutions during the polymerization time, resulting in a clearly defined interface. In principle, this technique can be extended to fabricate multifaceted surfaces with increased numbers of unique capture surfaces by designing microfluidic devices with more inlets, and employing this same technique.

Flow Capture and Release of Cells.

EpCAM-expressing prostate cancer cells (PC3) were captured by and released from anti-EpCAM functionalized PEGdiPDA gels in a continuous-flow microfluidic capture device. PC3 cells were captured on hydrogel surfaces within the device under flow (2 µL/min) and remained attached after rinsing the device with PBS (20 µL/min). UV light was focused through the 20× objective of an inverted epifluorescent microscope (λ=350-370 nm; Nikon TE2000) to erode a selective region of the gel under flow and release captured PC3 cells (FIG. 4a). During release under flow, captured cells began to detach from the gel as it was photodegraded; captured cells (FIG. 4a-i) first detached from the capture surface (FIG. 4a-ii), then rolled slowly along the surface (FIG. 4a-iii), and finally became entrained in the flow path and were removed from the device (FIG. 4a-iv). All cells in the region of UV light induced degradation released from the gel over the course of 30 seconds, while cells remained adhered to regions of the gel that were not photodegraded (FIG. 4b).

Current Studies and Future Directions.

This work has illustrated the utility of PEGdiPDA hydrogels for the capture and subsequent release of mammalian cells within microfluidic capture devices. Current work is focusing on the use of the multifaceted hydrogel films to capture multiple cell subtypes in single flow experiments and to demonstrate the ability to release and recover single cells. To employ these devices in clinically relevant settings, it is necessary to form capture surface with more efficient geometries, such as the herringbone topography.[19] Preliminary studies have shown that this geometry is amenable to the techniques in this paper (data not shown), but they have not been tested to capture rare cells from whole blood. Future work will apply PEGdiPDA herringbone devices to capture and recover rare cells from whole blood to demonstrate ability of these materials to perform in the presence of more complex biological fluids, which is important to test the clinical relevance of these devices. The culture of released cells will also be conducted to analyze the captured cells more fully downstream from the capture device. Specifically, the culture of individual circulating tumor cells would enable unprecedented experiments to be conducted on a relatively characterized population of cells. Capture and release of individual circulating tumor cells would enable clonal expansion for in vitro analysis, such as single cell genomics, and in vivo assessment of tumorigenicity.

CONCLUSION

A photodegradable hydrogel based microfluidic capture device was presented that enabled the unique ability to selectively capture and release mammalian cells under continuous flow. Acrylated-NeutrAvidin was included in the gel precursor solution to covalently link this reactive handle into the gel. The PEGdiPDA films were functionalized with biotinylated molecules, e.g., fluorescein and anti-EpCAM antibody, to quantify the degree of functionalization and to capture EpCAM expressing PC3 prostate cancer cells. Multifaceted films were fabricated pointing toward the ability to capture multiple cell subtypes within a single microfluidic device. Finally, PC3 cells were captured on hydrogel surfaces within the microfluidic device under continuous flow and subsequently released with UV light exposure. PEGdiPDA offer unique abilities in the development of microfluidic devices for cell sorting and diagnostics, in that cells can be captured and individually released for downstream culture and analysis.

The invention is not limited to the embodiments set forth in this disclosure for illustration, but includes everything that is within the scope of the claims. Furthermore, all documents cited in this disclosure are hereby incorporated by reference in their entirety and for all purposes as if fully set forth in this disclosure.

REFERENCES CITED

1. Evanko, D. Microfluidics and a garden hose. *Nat Meth* 5, 124-124 (2008).
2. Nagrath, S. et al. Isolation of rare circulating tumour cells in cancer patients by microchip technology. *Nature* 450, 1235-1239 (2007).
3. Cheng, X. et al. A microfluidic device for practical label-free CD4(+) T cell counting of HIV-infected subjects. *Lab Chip* 7, 170-178 (2007).
4. Cristofanilli, M. et al. Circulating tumor cells, disease progression, and survival in metastatic breast cancer. *New Engl J Med* 351, 781-791 (2004).
5. Braun, S. & Marth, C. Circulating tumor cells in metastatic breast cancer—toward individualized treatment? *N. Engl. J. Med.* 351, 824-826 (2004).

6. Stott, S. L. et al. Isolation and characterization of circulating tumor cells from patients with localized and metastatic prostate cancer. *Sci Transl Med* 2, 25ra23 (2010).
7. Maheswaran, S. et al. Detection of mutations in EGFR in circulating lung-cancer cells. *N. Engl. J. Med.* 359, 366-377 (2008).
8. Pappas, D. & Wang, K. Cellular separations: a review of new challenges in analytical chemistry. *Anal. Chim. Acta* 601, 26-35 (2007).
9. Wang, K., Marshall, M. K., Garza, G. & Pappas, D. Open-tubular capillary cell affinity chromatography: single and tandem blood cell separation. *Anal. Chem.* 80, 2118-2124 (2008).
10. Shah, A. M. et al. Biopolymer system for cell recovery from microfluidic cell capture devices. *Anal. Chem.* 84, 3682-3688 (2012).
11. Cooperstein, M. A. & Canavan, H. E. Biological cell detachment from poly(N-isopropyl acrylamide) and its applications. *Langmuir* 26, 7695-7707 (2010).
12. Hatch, A., Hansmann, G. & Murthy, S. K. Engineered alginate hydrogels for effective microfluidic capture and release of endothelial progenitor cells from whole blood. *Langmuir* 27, 4257-4264 (2011).
13. Machaca, K. Ca(2+) signaling, genes and the cell cycle. *Cell Calcium* 48, 243-250 (2010).
14. Kloxin, A. M., Tibbitt, M. W. & Anseth, K. S. Synthesis of photodegradable hydrogels as dynamically tunable cell culture platforms. *Nat Protoc* 5, 1867-1887 (2010).
15. Fairbanks, B. D., Schwartz, M. P., Bowman, C. N. & Anseth, K. S. Photoinitiated polymerization of PEG-diacrylate with lithium phenyl-2,4,6-trimethylbenzoylphosphinate: polymerization rate and cytocompatibility. *Biomaterials* 30, 6702-6707 (2009).
16. Hume, P. S. & Anseth, K. S. Inducing local T cell apoptosis with anti-Fas-functionalized polymeric coatings fabricated via surface-initiated photopolymerizations. *Biomaterials* 31, 3166-3174 (2010).
17. Kloxin, A. M., Kasko, A. M., Salinas, C. N. & Anseth, K. S. Photodegradable hydrogels for dynamic tuning of physical and chemical properties. *Science* 324, 59-63 (2009).
18. Tibbitt, M. W., Kloxin, A. M. & Anseth, K. S. Modeling Photodegradation in Optically Thick Polymer Networks for the Predictable Control of Network Evolution. *Macromolecules* In Review
19. Stott, S. L. et al. Isolation of circulating tumor cells using a microvortex-generating herringbone-chip. *P Natl Acad Sci USA* 107, 18392-18397 (2010).

We claim:

1. A photodegradable hydrogel for selectively capturing and releasing cells, said hydrogel produced by reacting in the presence of light:
   (a) a macromer having the chemical structure:
      L-P-B-P-L; wherein
      (i) L is a first linking moiety terminating with —$CH_xCH_y$, wherein the bond between the two carbon atoms is a covalent double or triple bond capable of taking part in an addition polymerization reaction, and wherein x is 0 or 1 and y is 1 or 2;
      (ii) P is a photolabile moiety; and
      (iii) B is a backbone structure comprising one or more repeating units that may be the same or different;
   (b) a cell-binding moiety attached to a second linking moiety terminating with:
      (i) —$CH_xCH_y$, wherein the bond between the two carbon atoms is a covalent double or triple bond capable of taking part in an addition polymerization reaction, and wherein x is 0 or 1 and y is 1 or 2, or
      (ii) —SH, wherein the —SH is capable of taking part in one or more of chain-growth polymerization, step-growth polymerization, or mixed-mode polymerization; and
   (c) a photoinitiator capable of producing free radicals in the presence of light, wherein the free radicals produced initiate a polymerization reaction, whereby the first linking moiety of the L groups of the macromer and the second linking moiety of the cell binding moiety are incorporated into polymer chains, whereby the macromer is cross-linked to form a hydrogel and the cell-binding moiety is incorporated into the hydrogel;
   wherein the cell-binding moiety further comprises a cell-binding agent, and
   wherein the cell binding moiety comprises avidin and the cell binding agent comprises a biotinylated antibody.

2. The hydrogel of claim 1, wherein the first linking moiety, the second linking moiety, or both comprise a terminal acrylate group.

3. The hydrogel of claim 1, wherein the photolabile moiety has the chemical structure:

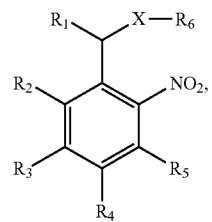

where X is O, N or S;
$R_1$ is selected from the group consisting of: hydrogen, straight-chain or branched C1-C10 alkyl, aryl, alkoxy, aryloxy or carboxy groups in which one or more carbon atoms can be independently optionally substituted with one or more heteroatoms, and one or more hydrogen atoms can be independently optionally substituted with hydroxyl, halogen or oxygen atoms;
$R_2$-$R_6$ are independently selected from the group consisting of: hydrogen; one or more polymerizable groups, one or more reactive end groups; straight chain, branched or cyclic C1-C20 alkyl, alkenyl, alkynyl groups in which one or more of the carbon atoms are optionally substituted with non-hydrogen substituents and wherein one or more C, CH or $CH_2$ moiety can be replaced with an oxygen atom, a nitrogen atom, an NR' group, or a S atom; and an optionally substituted aromatic or non-aromatic ring structure, wherein two or more R groups can be linked to form one or more rings which can contain one or more of the same or different heteroatoms;
one or more R groups can be optionally substituted with one or more substituent groups selected from halogens; nitro groups; cyano groups; isocyano groups; thiocyano groups; isothiocyano groups; azide groups; —$SO_2$ groups; —$OSO_3H$ groups; one or more optionally substituted straight-chain, branched or cyclic alkyl, alkenyl or alkynyl groups; OR'; —CO—OR'; —O—CO—R'; —N(R')$_2$; —CO—N(R')$_2$; —NR'—CO—OR'; —SR'; —SOR'; —$SO_2$—R'; —$SO_3$R'; —$SO_2$N(R')$_2$; —P(R')$_2$; —$OPO_3$(R')$_2$; and —Si(R')$_3$ wherein each R', independent of other R' in the substituent group can be a hydrogen, an optionally substituted straight-chain, branched or cyclic alkyl, alkenyl or alkynyl group wherein one or more C, CH or CH$_2$ groups therein can be replaced with an O atom, N atom, S atom or —NH group; an optionally substituted aromatic group, two or more R' groups can be linked together to form a ring which may contain one or more of the same or different heteroatoms; and R' can in turn be optionally substituted with one or more groups selected from the group consisting of halogens, nitro groups; cyano groups; isocyano groups; thiocyano groups; isothiocyano groups; azide groups; —SO$_2$ groups; —OSO$_3$H groups; straight-chain, branched or cyclic alkyl, alkenyl or alkynyl groups; halogenated alkyl groups; hydroxyl groups; alkoxy groups; carboxylic acid and carboxylic ester groups; amine groups; carbamate groups, thiol groups, thioether and thioester groups; sulfoxide groups, sulfone groups; sulfide groups; sulfate and sulfate ester groups; sulfonate and sulfonate ester groups; sulfonamide groups, sulfonate ester groups; phosphine groups; phosphate and phosphate ester groups; phosphonate and phosphonate ester groups; and alkyl-substituted silyl groups.

4. The hydrogel of claim 1, wherein the photolabile moiety has the chemical structure:

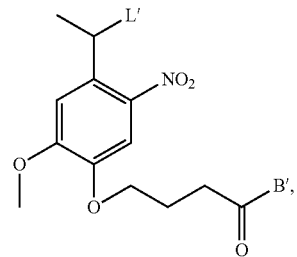

wherein L' is a covalent linkage to the first linking moiety, and wherein B' is a covalent linkage to the backbone structure.

5. The hydrogel of claim 1, wherein the backbone structure is selected from the group consisting of poly(ethylene glycol), poly(ethylene oxide), poly(vinyl alcohol), poly(styrene), poly(acrylate), poly(methacrylate), poly(vinylether), poly(urethane), polypropylene, polyester and polyethylene.

6. The hydrogel of claim 1, wherein the macromer has the chemical structure:

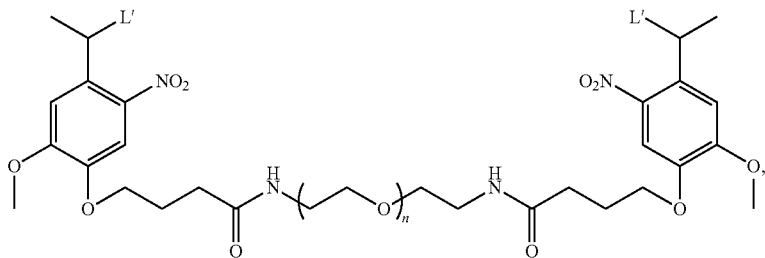

wherein L' is a covalently linkage to the first linking moiety.

7. The hydrogel of claim 6, wherein the macromer has the chemical structure:

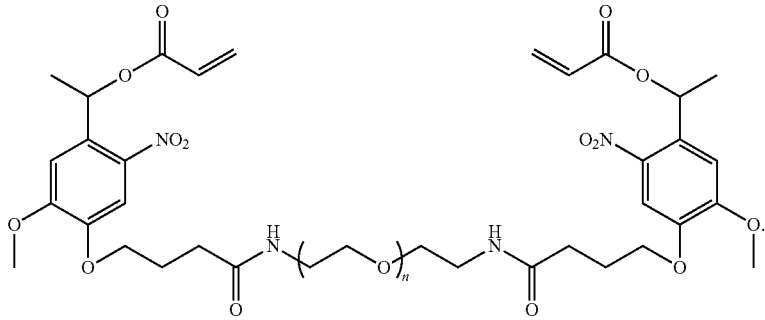

8. A method of capturing one or more cells from a fluid comprising:
(a) preparing a photodegradable hydrogel according to claim 1;
(b) contacting the hydrogel with a fluid comprising a biological sample that may contain one or more cells, wherein the one or more cells are capable of being captured by the cell-binding moiety, whereby the cells are captured by the cell-binding moiety.

9. A method of selectively capturing and releasing one or more cells in a fluid comprising the steps of:
  (a) preparing a photodegradable hydrogel according to claim 1;
  (b) contacting the hydrogel with a fluid comprising a biological sample that may contain one or more cells, wherein the one or more cells are capable of being captured by the cell-binding moiety; and
  (c) exposing the hydrogel to light, whereby the one or more cells are released from the hydrogel.

10. A kit for capturing one or more cells in a fluid comprising a photodegradable hydrogel prepared according to claim 1.

11. The hydrogel of claim 1, wherein the avidin comprises deglycosylated avidin.

12. The hydrogel of claim 1, wherein the antibody is an antibody which is capable of binding to circulating tumor cells (CTC).

13. The hydrogel of claim 1, wherein the photoinitiator is lithium phenyl-2,4,6-trimethylbenzoylphosphinate (LAP).

14. The hydrogel of claim 1, wherein the antibody is capable of binding to circulating tumor cells (CTC).

15. The hydrogel of claim 1, wherein the antibody is capable of binding to at least one of prostate cancer cells or lung cancer cells.

* * * * *